(12) United States Patent
Boiarski

(10) Patent No.: US 7,739,907 B2
(45) Date of Patent: Jun. 22, 2010

(54) CONTAINER FOR PHYSIOLOGICAL FLUIDS

(75) Inventor: Anthony A. Boiarski, Hilliard, OH (US)

(73) Assignee: Future Path Medical LLC, Columbus, OH (US)

( * ) Notice: Subject to any disclaimer, the term of this patent is extended or adjusted under 35 U.S.C. 154(b) by 0 days.

(21) Appl. No.: 11/947,555

(22) Filed: Nov. 29, 2007

(65) Prior Publication Data
US 2008/0156092 A1 Jul. 3, 2008

Related U.S. Application Data

(60) Provisional application No. 60/861,632, filed on Nov. 29, 2006.

(51) Int. Cl.
G01F 17/00 (2006.01)
(52) U.S. Cl. ...................... 73/149; 73/290 R; 73/304 C
(58) Field of Classification Search .................. 73/149, 73/304 C, 290 R
See application file for complete search history.

(56) References Cited

U.S. PATENT DOCUMENTS

| 3,942,167 | A | 3/1976 | McClintock |
| 4,051,431 | A | 9/1977 | Wurster |
| 4,343,316 | A | 8/1982 | Jespersen |
| 4,390,073 | A | 6/1983 | Rosen |
| 4,402,373 | A | 9/1983 | Comeau |
| 4,417,585 | A | 11/1983 | Frank |
| 4,447,939 | A | 5/1984 | Taylor |
| 4,448,207 | A | 5/1984 | Parrish |
| 4,449,969 | A | 5/1984 | Schweizer |

(Continued)

FOREIGN PATENT DOCUMENTS

EP 0 152 644 A2 8/1985

(Continued)

Primary Examiner—Hezron Williams
Assistant Examiner—Rodney T Frank
(74) Attorney, Agent, or Firm—Tarolli, Sundheim, Covell & Tummino LLP

(57) ABSTRACT

A container includes a chamber for containing fluid. At least one sensor is disposed within the chamber for sensing a property of fluid in the container. A unit that receives a signal from the sensor communicates with a device that displays the property of the fluid in the container. The container may include first and second chambers. A first sensor is disposed within the first chamber. The first sensor is in contact with fluid in the first chamber. The first sensor senses a volume of fluid in the first chamber. A second sensor is disposed within the second chamber. The second sensor is in contact with fluid in the second chamber. The second sensor senses a volume of fluid in the second chamber. A diverter may direct fluid from an inlet to a bottom portion of the chamber and prevents the fluid from contacting the sensor. A releasable device may prevent fluid from flowing from the first chamber to the second chamber. The releasable device permits fluid to flow from the first chamber into the second chamber upon release of the releasable device. An element of the sensor may have a first portion with an electrical resistance per unit length greater than an electrical resistance per unit length of a second portion of the element. A shunt resistor extending between lower portions of first and second elements of the sensor may have a resistance equal to approximately 0.08 times a resistance of the sensor when the chamber is empty.

44 Claims, 15 Drawing Sheets

U.S. PATENT DOCUMENTS

| | | | |
|---|---|---|---|
| 4,532,936 A | 8/1985 | LeVeen et al. | |
| 4,987,776 A * | 1/1991 | Koon | 73/304 C |
| 5,050,431 A | 9/1991 | McDonald | |
| 5,062,304 A | 11/1991 | Van Buskirk et al. | |
| 5,135,485 A | 8/1992 | Cohen et al. | |
| 5,148,708 A | 9/1992 | Murata et al. | |
| 5,226,313 A | 7/1993 | Murata et al. | |
| 5,312,379 A | 5/1994 | Rahe | |
| 5,501,102 A * | 3/1996 | Williamson | 73/304 R |
| 5,507,734 A | 4/1996 | Everett, Jr. et al. | |
| 5,603,238 A * | 2/1997 | Williamson | 73/304 R |
| 5,626,053 A * | 5/1997 | Williamson | 73/304 R |
| 5,627,523 A | 5/1997 | Besprozvanny et al. | |
| 5,882,931 A | 3/1999 | Petersen | |
| 6,010,454 A | 1/2000 | Arieff et al. | |
| 6,203,496 B1 | 3/2001 | Gael et al. | |
| 6,282,953 B1 * | 9/2001 | Benjey | 73/438 |
| 6,409,677 B1 | 6/2002 | Tulkki | |
| 6,433,695 B1 | 8/2002 | Kai et al. | |
| 6,595,051 B1 | 7/2003 | Chandler, Jr. | |
| 6,634,229 B1 | 10/2003 | Kazkaz et al. | |
| 6,829,927 B2 * | 12/2004 | Retterath et al. | 73/149 |
| 6,886,403 B2 * | 5/2005 | LaBarge et al. | 73/304 C |
| 6,938,476 B2 * | 9/2005 | Chesk | 73/290 R |
| 7,079,037 B2 * | 7/2006 | Ross et al. | 340/618 |
| 7,107,838 B2 * | 9/2006 | Chai et al. | 73/304 R |
| 7,161,361 B2 * | 1/2007 | Qu et al. | 324/690 |
| 7,174,780 B2 * | 2/2007 | Akahane et al. | 73/149 |
| 7,441,569 B2 * | 10/2008 | Lease | 141/95 |
| 7,506,541 B2 * | 3/2009 | Woodard et al. | 73/149 |
| 7,509,753 B2 * | 3/2009 | Nicosia et al. | 33/716 |
| 2001/0018206 A1 | 8/2001 | Delwiche et al. | |
| 2002/0161314 A1 | 10/2002 | Sarajarvi | |
| 2003/0029236 A1 * | 2/2003 | Morgan | 73/149 |
| 2003/0158707 A1 | 8/2003 | Doi | |
| 2004/0081585 A1 | 4/2004 | Reid | |
| 2005/0214161 A1 | 9/2005 | Gupta | |
| 2006/0212096 A1 | 9/2006 | Stevenson | |
| 2006/0229575 A1 | 10/2006 | Boiarski | |
| 2007/0157718 A1 * | 7/2007 | Woodard et al. | 73/149 |

FOREIGN PATENT DOCUMENTS

| | | |
|---|---|---|
| JP | 11-100075 A | 4/1999 |
| JP | 2002-156271 A | 5/2002 |

* cited by examiner

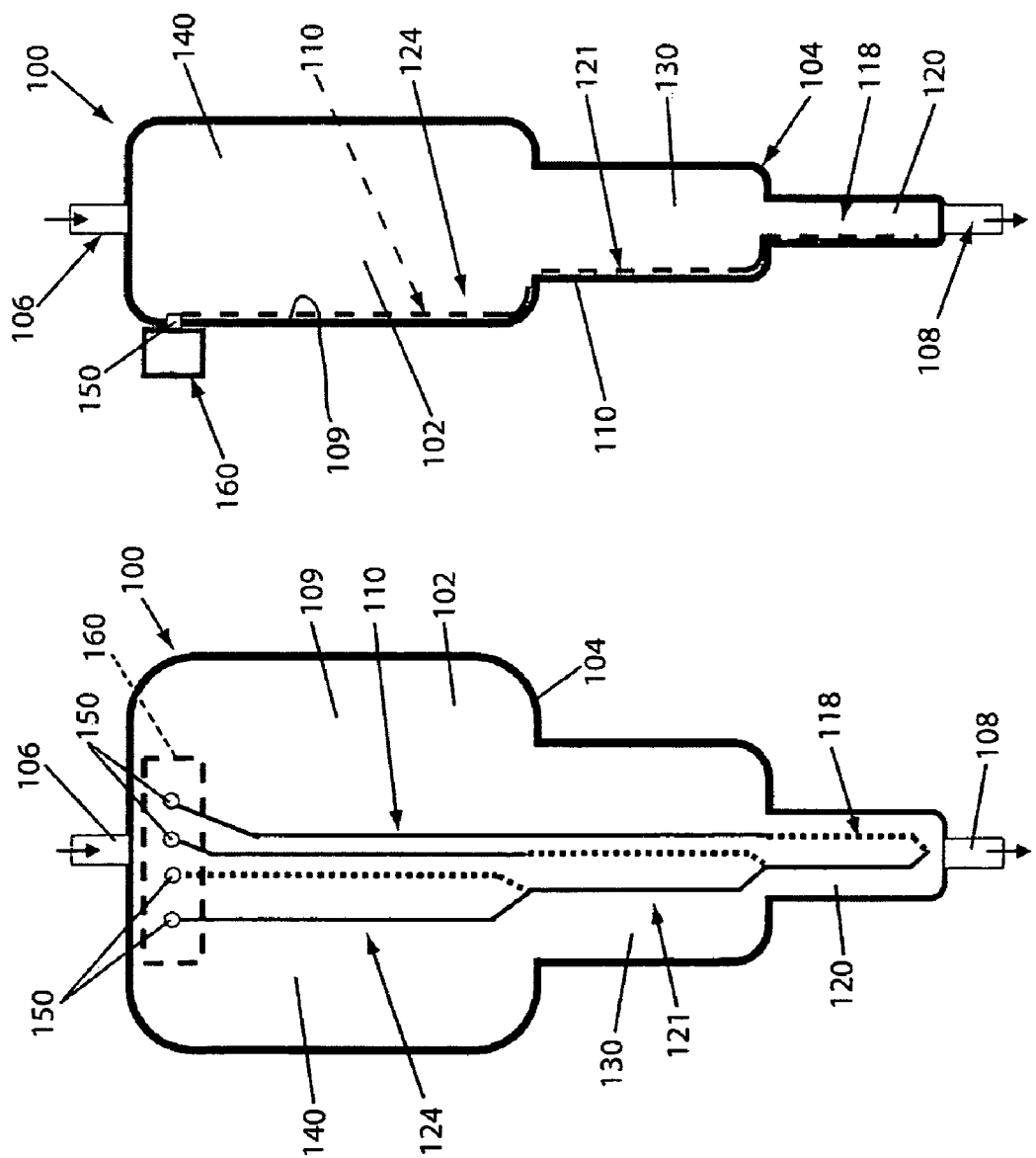

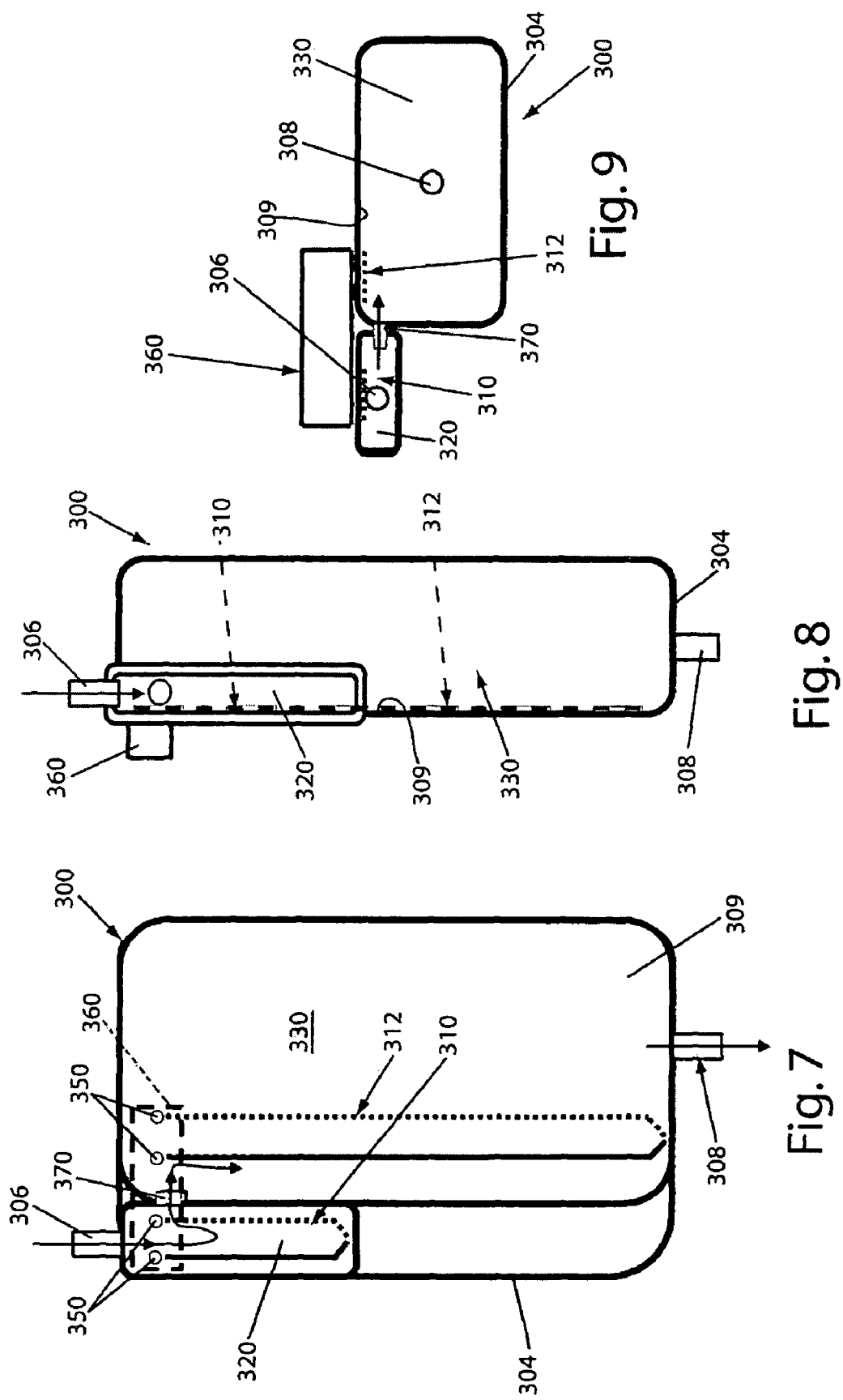

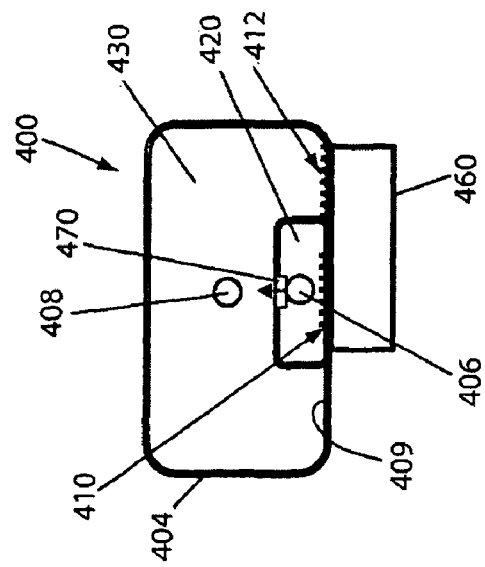
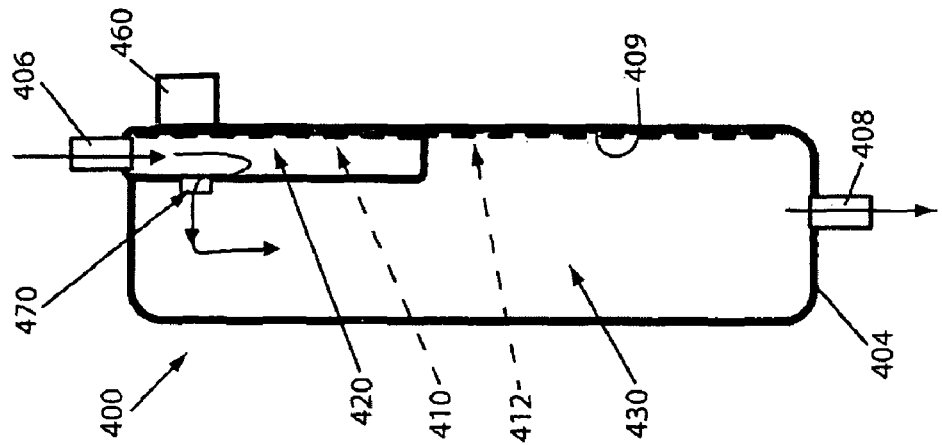
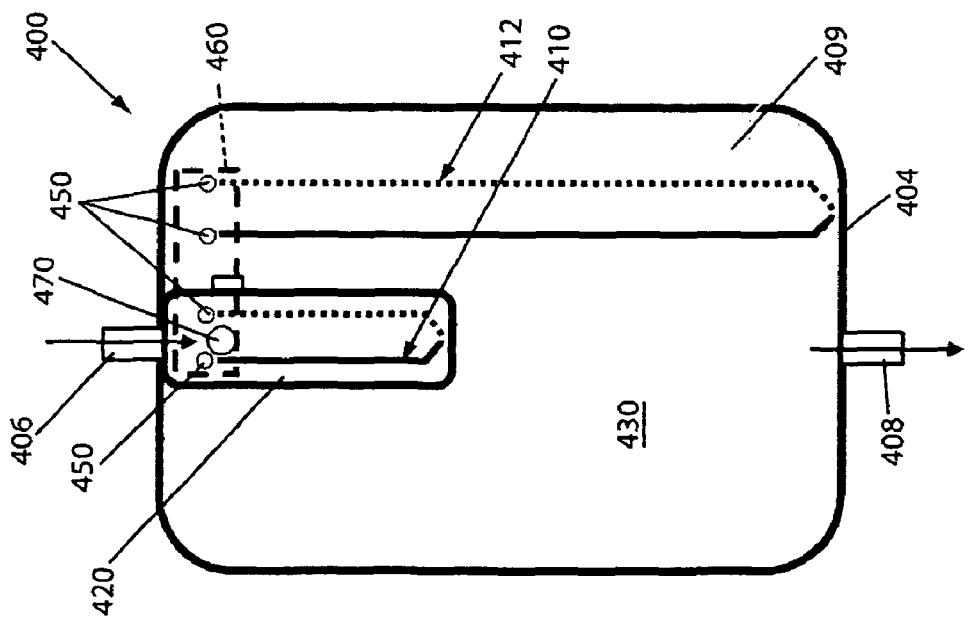

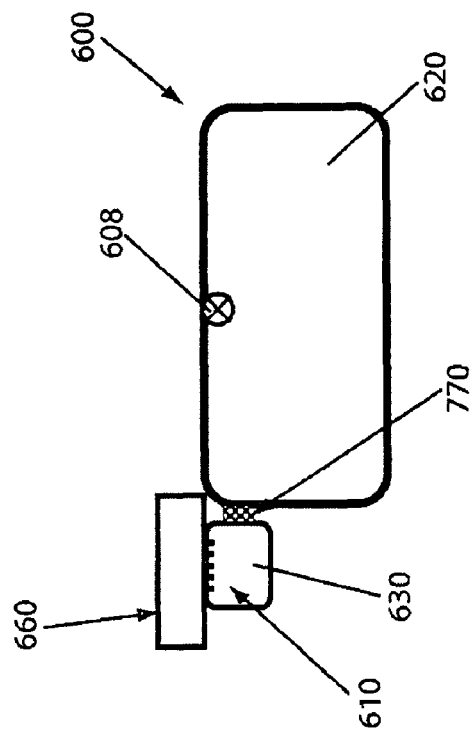
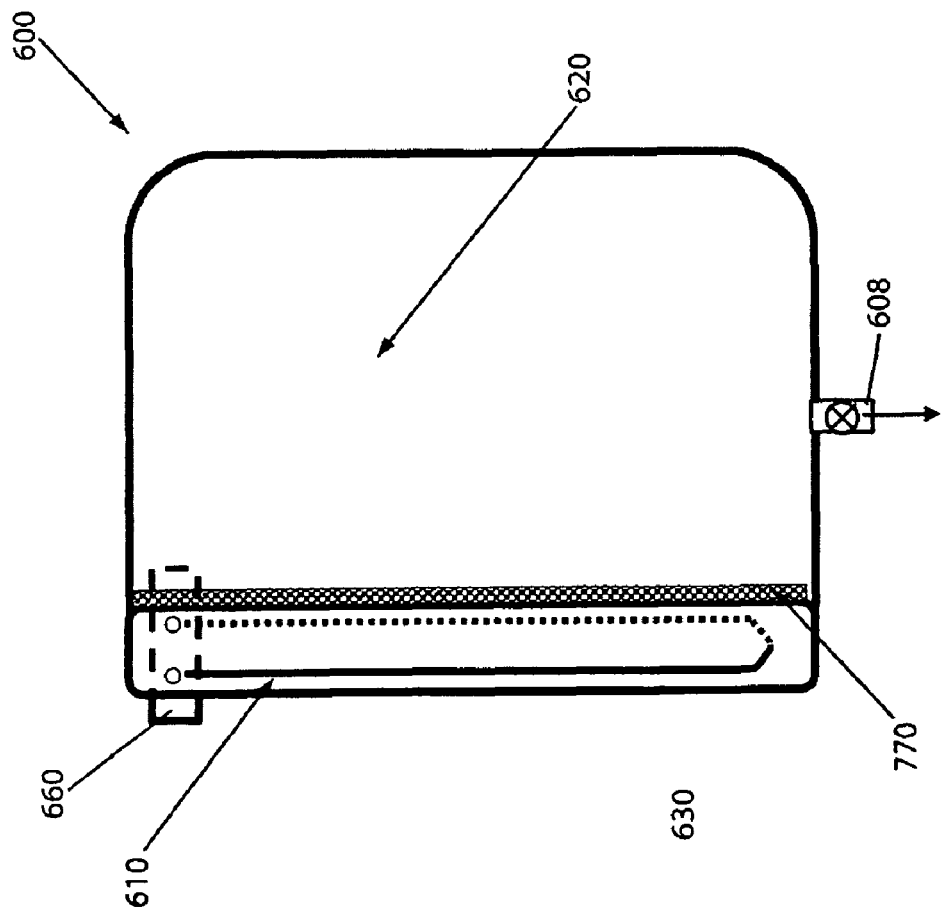
Fig. 22
Fig. 21

CONTAINER FOR PHYSIOLOGICAL FLUIDS

RELATED APPLICATION

This application claims priority from U.S. Provisional Patent application Ser. No. 60/861,632, filed Nov. 29, 2006, the subject matter of which is incorporated herein by reference.

FIELD OF THE INVENTION

The present invention relates to a container for physiological fluid, and more specifically, to a container that senses characteristics of the physiological fluid in the container.

BACKGROUND OF THE INVENTION

For a variety of reasons, it is desirable to supply fluids, such as electrolytes, to a patient or to collect physiological fluids from a patient in various settings including hospitals, nursing homes, private homes, or wheel chairs. For example, there are many instances of patient treatment where it is necessary to collect and determine, at all times, the accurate amount of expelled body fluids, such as urine, that is being released by the patient. It is, in fact, conventional in hospitals to collect urine from certain patients to measure and monitor urine output over time. This is routinely done for post-operative patients as well as those with urology disorders where, for example, urine output is directly related to renal function. This type of procedure for collecting, measuring and monitoring urine takes on added importance in some cases because sudden changes in urine flow, which can occur at any time, can indicate that there is a deteriorating clinical condition in the patient. Changes in urine output have also been correlated with changes in cardiac output.

The collection of urine and measurement of urine output (i.e., volume per unit time) are typically accomplished by first catheterizing the patient. In this procedure, the catheter is passed through the urethra of the patient into the bladder. The other end of the catheter is connected to a rigid collection container or a flexible vinyl drainage bag through a length of flexible tubing attached to a barbed fluid inlet port on the container. Typically the container is supported below the patient and from the patient's bed or other support system, such as a wheel chair, and urine drains by gravity from the patient through the flexible tubing and into the collection device. For patients who are mobile, this collection device is called a leg bag (flexible container), and for patients in a hospital bed it is called a urine collection device (flexible or rigid container). Hospital bed containers are usually 2,000 ml in capacity and leg bags are typically 1,000 ml, 800 ml, 700 ml, or even smaller. The measurement of container fill volume and urine output are typically accomplished by periodically draining the contents of the container into a graduated cylinder and manually recording the volume collected and the time it was collected. The urine output is then manually calculated and manually entered into the patient's record.

In addition to monitoring urine output as a function of time, the caregiver must monitor the collection container total volume to make sure it does not fill to capacity. This event can occur at unpredicted intervals and someone must empty the container before it can fill once again with urine. Further, patients can sometimes obstruct the flow of urine into the container by lying on and possibly crimping the drain tube. In this case, no urine appears in the container after an expected time period. Both a filled container and blocked input tube can cause urine backup into the bladder and a backup condition can have a deleterious effect on the patient's health. Also, the urine can spill onto the patient's bed linen and potentially cause/worsen various skin problems associated with being bedridden. For all the above reasons, caregivers must monitor the fill level in the collection container over time to make sure it does not overfill or is not properly filling. This manual process is time consuming (i.e., costly) and could also lead to problems associated with handling of urine, which is a biohazard.

U.S. Patent Publication No. 2006/0229515 describes a device for continuously and automatically monitoring the fluid level in collection and delivery containers. A disposable sensor is placed inside the container to measure fluid fill level. A reusable electronic device is attached to the outside of the container to continuously record sensor changes and to wirelessly transmit fill level information to external receiver/data processor/display devices. A connection device through the container wall allows the external electronic device to interface with the internal sensor. The device helps save time, minimize urine backup and also reduce the amount of caregiver-patient urine contact.

An advantage of the device described in U.S. Patent Publication No. 2006/0229515 is that the container could have a variable cross-sectional area typical of flexible, low-cost vinyl bags used in the medical industry. It is desirable to improve the accuracy of fluid level measurements, especially for urine collection devices used in the hospital's intensive care unit (ICU) where accurate initial urine flow rates are considered much more important. It is also desirable to improve measurement accuracy at low container fill volumes.

SUMMARY OF THE INVENTION

A container of the present invention includes a chamber for containing fluid. A sensor is disposed within the chamber for sensing a property of fluid in the container. A unit that receives a signal from the sensor communicates with a device that displays the property of the fluid in the container.

In another aspect of the present invention, a container for fluid includes a first chamber for containing fluid and a second chamber for containing fluid. A first sensor is disposed within the first chamber. The first sensor is in contact with fluid in the first chamber. The first sensor senses a volume of fluid in the first chamber. A second sensor is disposed within the second chamber. The second sensor is in contact with fluid in the second chamber. The second sensor senses a volume of fluid in the second chamber.

In another aspect of the present invention, a container for fluid includes a chamber for containing fluid. An inlet directs fluid into the chamber. A sensor disposed within the chamber senses a volume of fluid in the chamber. A diverter directs fluid from the inlet to a bottom portion of the chamber and prevents the fluid from contacting the sensor.

In another aspect of the present invention, a container for fluid includes a first chamber for containing fluid and a second chamber for containing fluid. A sensor in the second chamber senses a property of fluid in the second chamber. A releasable device prevents fluid from flowing from the first chamber to the second chamber. The releasable device permits fluid to flow from the first chamber into the second chamber upon release of the releasable device.

In another aspect of the present invention, a container for fluid includes a chamber for containing fluid. A sensor senses a volume of fluid in the chamber. The sensor has first and second elements extending from an upper portion of the chamber to a lower portion of the chamber. The first element has a first portion with an electrical resistance per unit length greater than an electrical resistance per unit length of a second portion of the first element.

In another aspect of the present invention, a container for fluid includes a chamber for containing fluid. A sensor senses a volume of fluid in the chamber. The sensor has first and second elements extending from an upper portion of the chamber to a lower portion of the chamber. A shunt resistor extends between the lower portions of the first and second elements. The shunt resistor has a resistance equal to approximately 0.08 times a resistance of the sensor when the chamber is empty.

BRIEF DESCRIPTION OF THE DRAWINGS

The accompanying drawings and figures, which are incorporated in and form a part of the specification, schematically illustrate preferred embodiments of the invention and, together with the general description given above and detailed description of the preferred embodiments and examples given below, serve to explain the principles of the invention.

FIG. 1 is a schematic view of a first exemplary embodiment of a container of the present invention;

FIG. 2 is a schematic side view of the container of FIG. 1;

FIG. 3 is a schematic top view of the container of FIG. 1;

FIG. 7 is a schematic view of a third exemplary embodiment of a container of the present invention;

FIG. 8 is a schematic side view of the container of FIG. 7;

FIG. 9 is a schematic top view of the container of FIG. 7;

FIG. 10 is a schematic view of a fourth exemplary embodiment of a container of the present invention;

FIG. 11 is a schematic side view of the container of FIG. 10;

FIG. 12 is a schematic top view of the container of FIG. 10;

FIG. 21 is a schematic view of a ninth exemplary embodiment of a container of the present invention;

FIG. 22 is a schematic top view of the container of FIG. 21;

DETAILED DESCRIPTION OF EXEMPLARY EMBODIMENTS OF THE INVENTION

Figure 6:
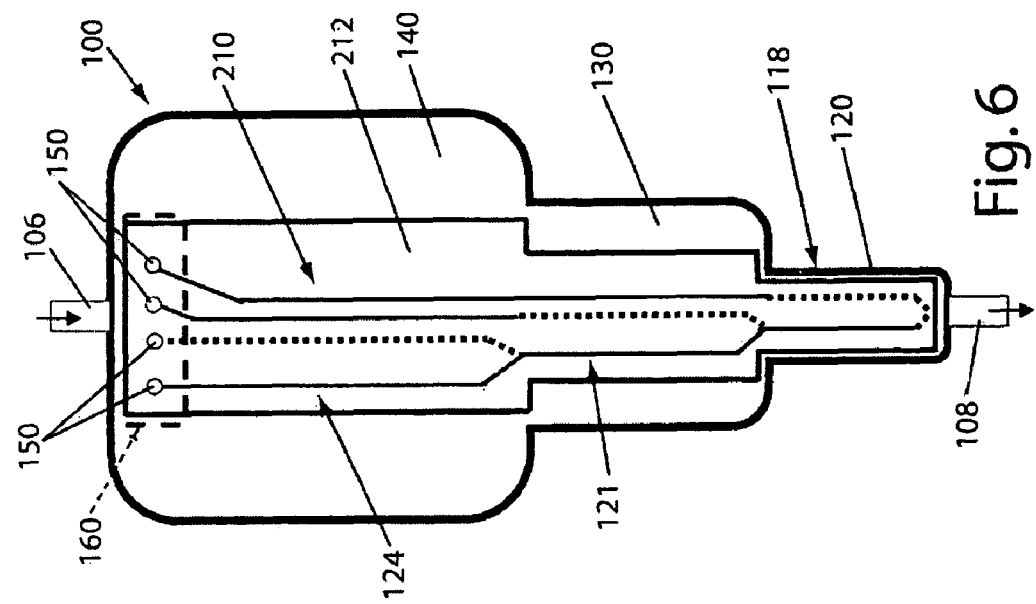
FIG. 6 is a schematic front view of the container of FIG. 5.

A container 100 constructed in accordance with a first exemplary embodiment of the present invention is shown in FIGS. 1-4. The container 100 may be a rigid or flexible container having a wall 104 that forms an overall interior chamber 102 that has a total volume $V_T$. Fluid, such as physiological fluid, flows into the chamber 102 through an inlet 106. The physiological fluid may be urine from an indwelling urinary catheter or wound drainage fluid from a trans-abdominal drainage catheter. An outlet valve 108 may be used to allow fluids to flow from the container 100 for disposal or for delivery to a patient.

The container 100 includes a plurality of interconnected regions or chambers 120, 130, and 140. Although three chambers 120, 130 and 140 are shown, it is contemplated that the container 100 may have any desired number of chambers. Each chamber 120, 130, and 140 has a different volume (i.e., V1, V2, V3) and the volume of the chambers adds up to a total volume of $V_T$=V1+V2+V3. The lower chamber 120 has a smaller volume than the chambers 130 and 140. The chamber 130 has a smaller volume than the chamber 140. Fluid entering the container 100 flows (by gravity) to the lower chamber 120 and starts to fill the smallest volume chamber 120. Once chamber 120 is filled, the fluid starts filling the second chamber 130. The upper chamber 140 begins to fill when the chamber 130 is filled.

A sensor 110 is located within the chamber 102 of container 100. The sensor 110 may be formed on an inner surface 109 of the wall 104. The sensor 110 contacts fluid within the container 100. The sensor 110 senses the volume of fluid (i.e., fill level) within the container 100.

The sensor 110 is used to measure the fill level of the fluid in the container 100. The sensor 110 connects to a plurality of electrical interface devices 150 at the top of the container 100. The interface devices 150 conduct electrical signals from the sensor 110 to a reusable electronic unit 160 that attaches to the container 100. Snap connectors (not shown) may be used to connect the electronic unit 160 to the container 100 as described in U.S. Patent Publication No. 2006/0229515, which is incorporated herein in its entirety. Electronic unit 160 processes the sensor signals to provide physiological information of interest, such as the volume of fluid in the container 100. Electronic unit 160 may wirelessly transmit the information to a remote unit (not shown) for display and analysis.

The sensor 110 (FIG. 4) includes a plurality of electrically conductive elements 111, 113, and 115 and a plurality of electrically resistive elements 112, 114, and 116. The conductive elements 111, 113, and 115 may be highly conductive (approximately zero resistance). The resistive elements 112, 114, and 116 may have a high electrical resistance (e.g., approximately 10,000 ohms per inch). The conductive elements 111, 113, and 115 may be a metal-based material (e.g., silver) that is printed on the inner surface 109 of the container 100. The resistive elements 112, 114, and 116 may be a carbon ink material printed on the inner surface 109 of the container 100. The conductive elements 111, 113, and 115 and the resistive elements 112, 114, and 116 may be printed on the inner surface 109 of the container 100 using ink-jet printing or screen printing.

A lower portion 117 of conductive element 111 extends from point A to point B in the container 100 and the resistive element 112 extends from point A to point E. The lower portion 117 and the resistive element 112 are connected at point A. The conductive element 111 and the resistive element 112 extend from adjacent the bottom of the container 100 to adjacent a top of the chamber 120. The lower portion 117 of conductive element 111 and the resistive element 112 form a first U-shaped fill level sensor 118 that senses the volume of fluid in the chamber 120 at the bottom of container 100. The conductive elements 111 and 113 conduct electrical signals from the lower portion 117 of the element 111 and the resistive element 112 to the electrical interface devices 150 at the top of the container 100.

An intermediate portion 119 of the conductive element 111 extends from point B to point C and resistive element 114 extends from point B to point G. The intermediate portion 119 and the resistive element 114 are connected at point B. The intermediate portion 119 of the conductive element 111 and the resistive element 114 extend from adjacent a bottom of the chamber 130 to adjacent a top of the chamber 130. The intermediate portion 119 of the conductive element 111 and the resistive element 114 form a second U-shaped fill level sensor 121 that senses the volume of fluid in the second chamber 130. Conductive elements 115 and 111 conduct signals from the second sensor 121 to the interface devices 150 at the top of the container 100.

An upper portion 122 of conductive element 111 extends from point C to point D and resistive element 116 extends from point C to point I. The upper portion 122 and the resistive element 116 are connected at point C. The upper portion 122 of the conductive element 111 and the resistive element 116 extend from adjacent a bottom of the chamber 140 to adjacent a top of the chamber 140. The upper portion 122 of conductive element 111 and the resistive element 116 form a third U-shaped fill level sensor 124 that senses the volume of fluid in chamber 140 at the top of container 100. The upper portion 122 of the conductive element 111 and the resistive element 116 conduct electrical signals from the third sensor 124 to the interface devices 150.

The chamber 120 is shorter than chamber 130. Therefore, the first sensor 118 is shorter than the second sensor 121. The chamber 130 is shorter than the chamber 140. Thus, the sensor 121 is shorter than the sensor 124. The chambers 120, 130 and 140 and sensors 118, 121 and 124 may have any desired lengths.

Fill level in the chambers 120, 130 and 140 is determined by measuring the resistance of a continuous, carbon-electrode resistor path of the sensors 118, 121 and 124. As the fluid level changes in the container 100, more or less of the elements 111-116 are shorted out, thereby changing the sensor resistance, $R_S$. Sensor resistance is measured by using a series circuit containing the sensor resistor, a load resistor, $R_L$, and an input voltage source, Vo. The voltage source can be an alternating voltage waveform with a peak-to-peak value of Vo(Pk–Pk) at some frequency, f, or it can be a pulsed voltage with a peak of Vo(Pk) and a short pulse width, Δt.

The current in this series circuit, $I_S$, can be written, according to Ohm's Law, as:

$$I_S = Vo/(R_S + R_L) \qquad \text{Eq. (1)}$$

As $R_S$ changes (due to change in fill level), then $I_S$ changes.

The sensor resistance changes with fluid level or liquid height, h, of the fluid over a sensor length, L, as follows:

$$R_S = R_S(0) \cdot (1 - h/L) \qquad \text{Eq. (2)}$$

Where, $R_S(0)$ is the constant initial sensor resistance. The load resistor is usually picked to match the sensor resistor, so $R_L \cong R_S(0)$. Therefore, Eq (1) can be written as follows:

$$I_S = Vo/[R_S(0) \cdot (2 - h/L)] \qquad \text{Eq. (3)}$$

Again, according to Ohms Law, the signal voltage, $E_S$, across the load resistor $R_L$ (where $R_L \cong R_S(0)$) is:

$$E_S = I_S \cdot R_L = Vo/(2 - h/L) \qquad \text{Eq. (4)}$$

For h=0 (empty bag), $E_S = E_{S0} = Vo/2$. Therefore, Eq (4) can be written:

$$E_S/E_{S0} = 1/(1 - h/2L) \qquad \text{Eq. (5)}$$

Eq (5) indicates that $E_S$ varies from $E_{S0}$ to $2E_{S0}$ as h varies from 0 to L, so the maximum change in the signal voltage is 100% of the original voltage.

Fill level measurement accuracy can be determined by calculating the slope of $E_S/E_{S0}$, which involves differentiating Eq (5) with respect to the fill height, h, to obtain the following:

$$d/dh[E_S/E_{S0}] = (\tfrac{1}{2}L) \cdot (1 - h/2L)^{-2} \qquad \text{Eq. (6)}$$

Eq (6) can be used to estimate that the accuracy varies over the range from (½L) for h=0 to (2/L) for h=L. Therefore, the greater the sensor length (larger L), for a given container length, the less accurate the measurement. Also, the accuracy is less at lower volumes and improves at higher volumes.

Volume measurement accuracy can be estimated by calculating the change in signal per unit change in fill volume, V, as follows:

$$d/dV[E_S/E_{S0}] = d/dh[E_S/E_{S0}] \cdot dh/dV \qquad \text{Eq. (7)}$$

For a typical container, V=h·Aavg, where Aavg is the average cross-sectional container area over the length of the sensor. Substituting the derivative dh/dV and Eq (6) into Eq (7) results in the following equation for the volume measurement accuracy:

$$d/dV[E_S/E_{S0}] = (1/A\text{avg}) \cdot ((\tfrac{1}{2}L) \cdot (1 - h/2L)^{-2} \qquad \text{Eq. (8)}$$

Since Aavg*L=Vavg, where Vavg is the average volume over the sensor length, then the volume measurement accuracy can be written:

$$d/dV[E_S/E_{S0}] = (\tfrac{1}{2}V\text{avg}) \cdot (1 - h/2L)^{-2} \qquad \text{Eq. (9)}$$

Equation (9) indicates that the volume measurement accuracy decreases the larger the volume to be measured with a given sensor length. Therefore, accuracy may improve if multiple smaller container volumes, with multiple sensors, are used instead of one larger container volume with one sensor.

The container 100 permits accurate measurement of the volume of fluid in the container because the volumes of the chambers 120, 130, and 140 are smaller than the total volume and three individual relatively short sensors are used to measure the fill level rather than one relatively long sensor. Also, the accuracy is highest for the fluid that initially enters the container 100 since the fluid first goes into the smallest volume chamber 120 with the shortest sensor 118.

Figure 5:
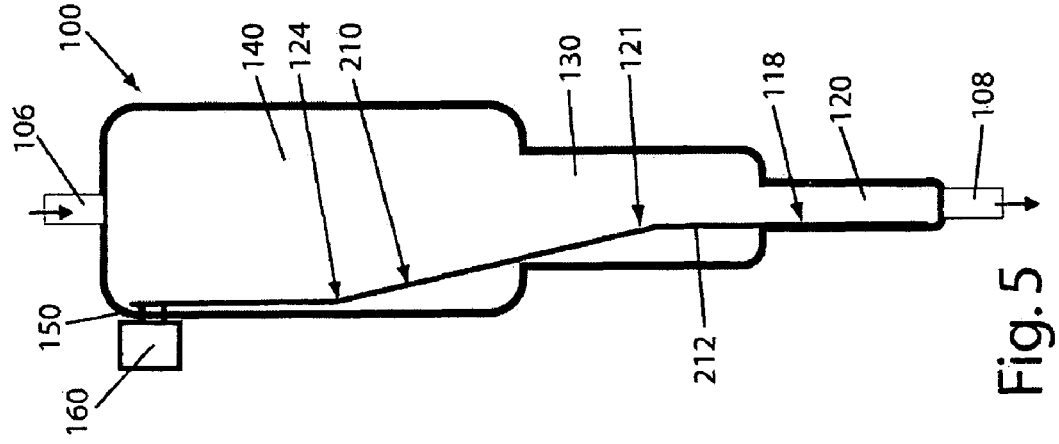
FIG. 5 is a schematic side view of a second exemplary embodiment of a container of the present invention.
Figure 4:
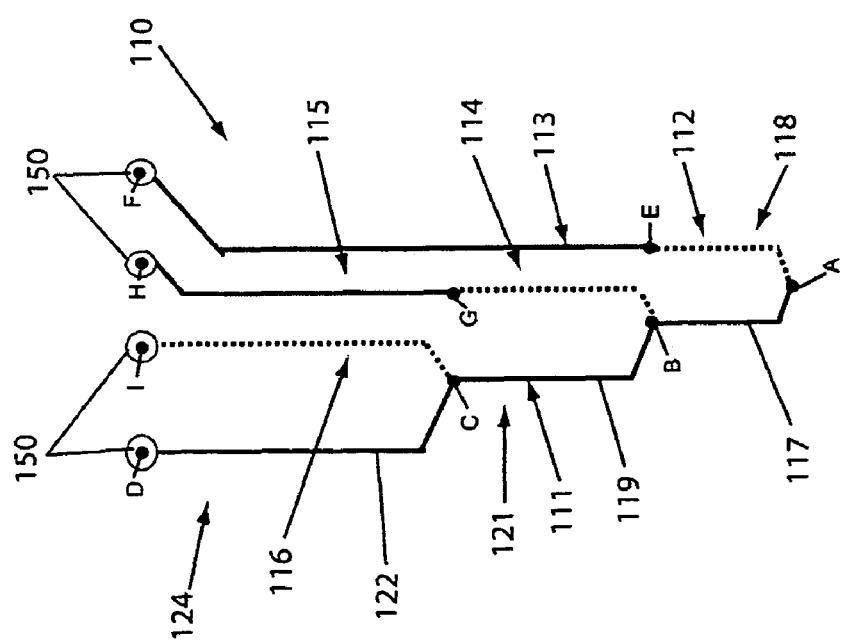
FIG. 4 is a schematic view of a sensor of the container of FIG. 1.

A second exemplary embodiment of a container constructed in accordance with the present invention is illustrated in FIGS. 5 and 6. The embodiment shown in FIGS. 5-6 is substantially similar to the embodiment shown in FIGS. 1-4. Accordingly, the same reference numbers will be used to designate similar components in FIGS. 5 and 6. A sensor 210 extends within the container 100. The sensor 210 is not formed on the wall 104 of the container 100. The elements of the sensor 210 are printed on a strip of flexible material 212 (e.g. polyester). The strip of material 212 hangs in the container 100 so that the first sensor 118 is located in the chamber 120, the second sensor 121 is located in the chamber 130 and the third sensor 124 is located in the chamber 140. If the container 100 is flexible, the sensor 210 will not stretch with the flexible container as fluid enters the container.

A container 300 constructed in accordance with a third exemplary embodiment of the present invention is shown in FIGS. 7-9. The container 300 may be rigid or flexible. The container 300 includes first and second chambers 320 and 330. The container 300 has walls 304 defining the chambers 320 and 330. The chambers 320 and 330 are formed adjacent to each other with an orifice 370 connecting the chambers. The chamber 320 is smaller than the chamber 330. The two chambers 320 and 330 have a total volume $V_T$. An inlet 306 to the container 300 communicates with the chamber 320. An outlet valve 308 communicates with the chamber 330 and permits fluid to flow from the container 300. It is contemplated that the chamber 320 may also have an outlet valve (not shown) for permitting fluid to flow from the chamber 320.

A first sensor 310 is located within the chamber 320. A second sensor 312 is located within the chamber 330. The sensors 310 and 312 are in contact with fluid within the chambers 320 and 330 in order to sense the volume of fluid (i.e., fill level) within the chambers. The sensors 310 and 312 are shown formed on an interior surface 309 of the wall 304 of the container 300. The sensor 310 is shorter in length than the sensor 312. The sensor 310 extends along the length of the chamber 320. The sensor 312 extends along the length of the chamber 330.

The first and second sensors 310 and 320 may be generally similar to the sensor 124 described in the embodiment of FIGS. 1-4. The sensors 310 and 312 may be formed from a high-resistance material. The sensors 310 and 312 are connected to a plurality of low-conductivity electrical interface devices 350 at the top of the container 300. The devices 350 conduct signals from the sensors 310 and 312 to a reusable electronic unit 360 that attaches to the container 300 as described in connection with the first exemplary embodiment. The unit 360 may be generally similar to the unit 160 described in the embodiment of FIGS. 1-4.

The chambers 320 and 330 have different volumes V1 and V2. The total volume of the container 300 equals the sum of the volumes of the chambers 320 and 330, $V_T=V1+V2$. Fluid entering the container 300 (by gravity) goes into the first chamber 320 and starts to fill the smaller volume chamber. Once the chamber 320 is filled with a volume V1 of fluid, the fluid flows into the second chamber 330 through the interconnecting orifice 370. If nothing is done to interrupt the collection process, the chamber 320 remains filled and fluid flows into the second chamber 330. The container 300 permits accurate measurement of the volume of fluid in the container because the volumes of the chambers 320 and 330 are smaller than the total volume and a relatively short sensor 310 is used to sense the fill level in the chamber 320. Also, the accuracy is highest for the fluid that initially enters the container 300 since the goes into the smallest volume chamber 320 with the shortest sensor 310.

After a period of filling (not necessarily filling to full capacity), the chamber 320 can be emptied into the chamber 330 by squeezing the chamber 320 or tipping the chamber 320 from a normal vertical position shown in FIG. 7 so that fluid from chamber 320 enters the chamber 330. Emptying the chamber 320 allows new fluid to enter chamber 320 for more accurate measurement of fluid entering the container 300.

The container 300 permits accurate measurement of the volume of fluid in the container because the volumes of the chambers 320 and 330 are smaller than the total volume and a short sensor is used to measure the fill level in the chamber 320. Also, the accuracy is highest for the first fluids to enter the container 300 since the first fluid that enters the container goes into the chamber 320 with the smallest volume chamber and the shortest sensor. Also, by manually emptying the first chamber 320, the highest accuracy can be maintained throughout the fluid collection process while the two sensors allow for continuous electronic tracking of the total collected volume. Two volume outputs can be displayed, namely: V1 (highest accuracy) and $V_T=V1+V2$ (lower accuracy).

A container 400 constructed in accordance with a fourth exemplary embodiment of the present invention is shown in FIGS. 10-12. The container 400 may be rigid or flexible. The container 400 includes first and second chambers 420 and 430. The container 400 may have walls 404 forming the chambers 420 and 430. The chamber 420 is located within the chamber 430. An orifice 470 connects the chambers 420 and 430. The chamber 420 is smaller than the chamber 430. The two chambers 420 and 430 have a total volume $V_T$. An inlet 406 to the container 400 communicates with the chamber 420. An outlet valve 408 communicates with the chamber 430 and permits the flow of fluid from the container 400. It is contemplated that the chamber 420 may also have an outlet valve for permitting the flow of fluid from the chamber 420.

A first sensor 410 is located within the chamber 420. A second sensor 412 is located within the chamber 430. The sensors 410 and 412 are in contact with fluid within the chambers 420 and 430 in order to measure the volume of fluid (i.e., fill level) within the chambers. The sensors 410 and 412 may be formed on an interior surface 409 of the wall 404 of the container 400. The sensor 410 is shorter in length than the sensor 412. The sensor 410 extends along the length of the chamber 420. The sensor 412 extends along the length of the chamber 430.

The first and second sensors 410 and 412 may be generally similar to the sensor 124 described in the embodiment of FIGS. 1-4. The sensors 410 and 412 may be formed from high-resistance material and are connected to a plurality of low-conductivity electrical interface devices 450 at the top of the container 400. The devices 450 conduct signals from the sensors 410 and 412 to a reusable electronic unit 460 that attaches to the container 400 as described in connection with the first exemplary embodiment. The unit 460 may be generally similar to the unit 160 described in the embodiment of FIGS. 1-4.

The chambers 420 and 430 have different volumes V1 and V2. The volume of the container 400 equals the sum of the volumes of the chambers 420 and 430, $V_T=V1+V2$. Fluid entering the container 400 (by gravity) goes into the first chamber 420 and starts to fill the smaller volume chamber. Once the chamber 420 is filled with a volume V1 of fluid, the fluid flows into the second chamber 430 through the interconnecting orifice 470. If nothing is done to interrupt the collection process, the chamber 420 remains filled and fluid flows into the second chamber 430. The container 400 permits accurate measurement of the volume of fluid in the container because the volumes of the chambers 420 and 430 are smaller than the total volume and a relatively short sensor 410 is used to sense the fill level in the chamber 420. Also, the accuracy is highest for the fluid that initially enters the container 400 since the fluid goes into the smallest volume chamber 420 with the relatively short sensor 410.

After a period of filling (not necessarily filling to full capacity), the chamber 420 can be emptied into the chamber 430 by squeezing the chamber 420 or tipping the chamber 420 from a normal vertical position shown in FIG. 10 so that fluid from chamber 420 enters the chamber 430. Emptying the chamber 420 allows new fluid to enter chamber 420 for more accurate measurement of the volume of new fluid entering the container 400.

The container 400 permits accurate measurement of the volume of fluid in the container because the volumes of the chambers 420 and 430 are smaller than the total volume and a short sensor is used to measure the fill level in the chamber 420. Also, the accuracy is highest for the first fluids to enter the container 400 since the first fluid that enters the container goes into the chamber 420 with the smallest volume chamber and the shortest sensor. Also, by manually emptying the first chamber 420, the highest accuracy can be maintained throughout the fluid collection process while the two sensors allow for continuous electronic tracking of the total collected volume. Two volume outputs can be displayed, namely: V1 (highest accuracy) and $V_T$=V1+V2 (lower accuracy).

The chamber 420 may be made of molded, rigid, thin-walled plastic with an integral inlet 406. The container 400 may be RF welded and sealed similar to methods used to weld and seal plastic inlet/outlet parts on current vinyl collection bags as known in the art. A rigid chamber 420 may provide further accuracy in fill-level measurements.

Figure 14:
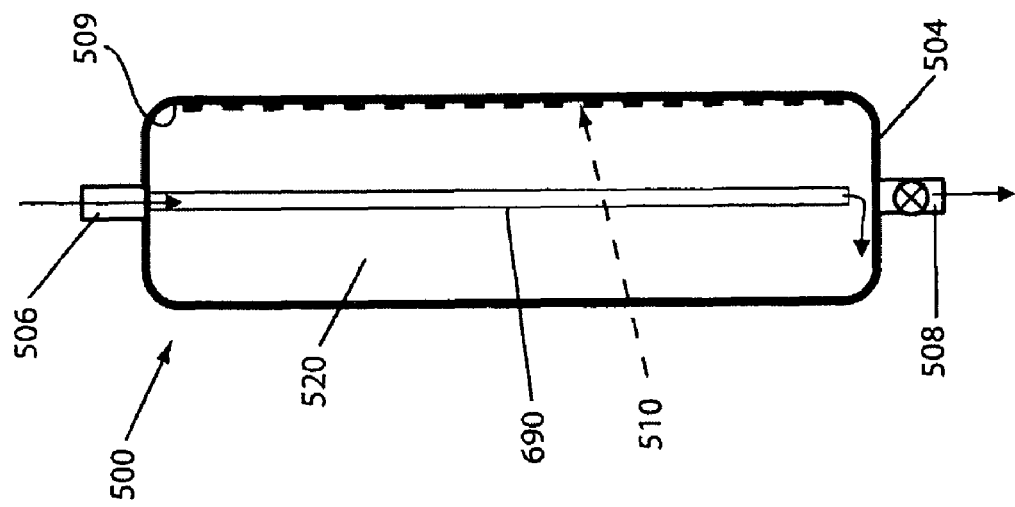
FIG. 14 is a schematic side view of the container of FIG. 13.
Figure 13:
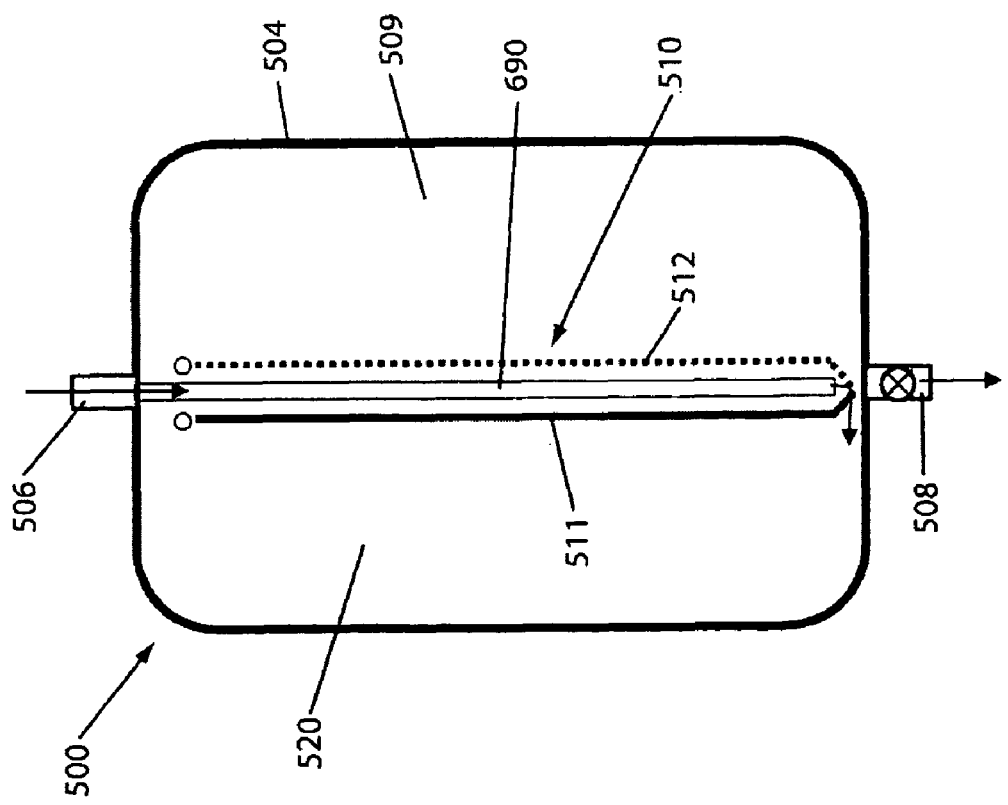
FIG. 13 is a schematic view of a fifth exemplary embodiment of a container of the present invention.

A container 500 constructed in accordance with a fifth exemplary embodiment of the present invention is shown in FIGS. 13 and 14. The container 500 includes a chamber 520 with an inlet 506. The container 500 may be rigid or flexible. A diverter 690, such as a tube, located inside the container 500, directs flow from the inlet 506 to the bottom of the container 500. Thus, the input fluid flow does not contact the sensor 510 that is attached to an interior surface 509 of a wall 504. The tube 690 may extend through a generally central portion of the container 500. Accordingly, the diverter 690 prevents a temporary short from occurring between the elements 511 an 512 of the sensor 510 causing an erroneous fill measurement to be sensed. If the container 500 is flexible, the diverter 690 prevents walls of the container from touching each other in the region of the sensor 510. Thus, the tube 690 prevents an erroneous fill measurement to be sensed due to wall contact that may cause any fluids on the walls opposite the sensor 510 to contact the resistive elements of the sensor 510 resulting in the erroneous fill-level measurement conditions.

Figure 16:
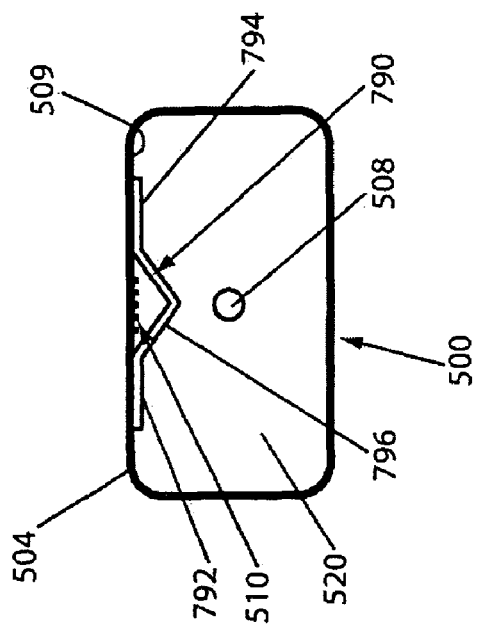
FIG. 16 is a schematic top view of the container of FIG. 15.
Figure 15:
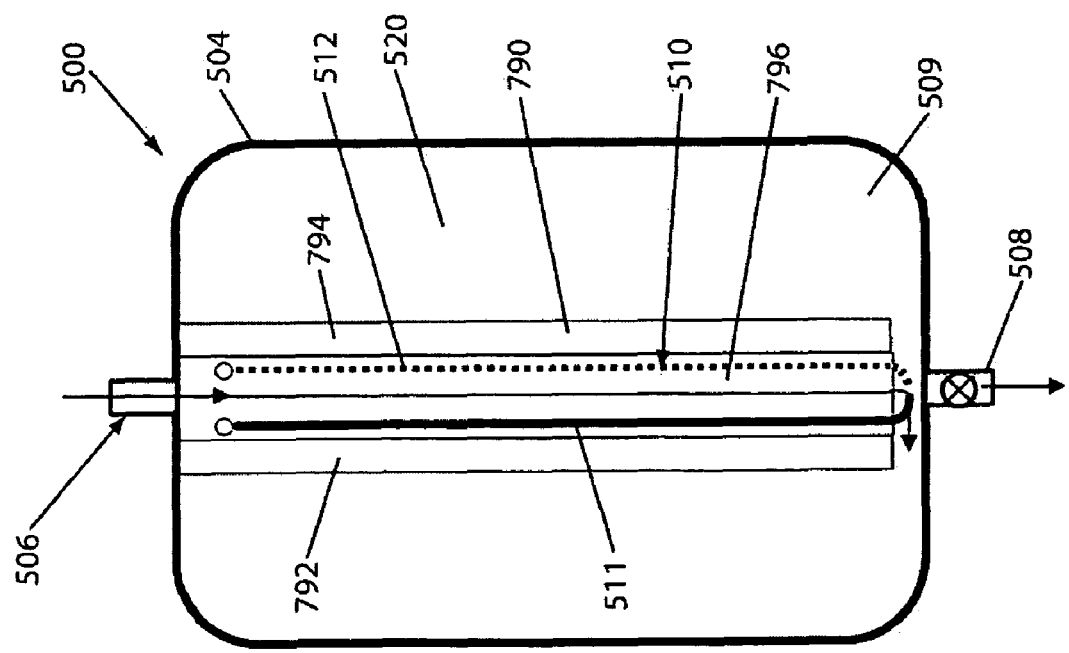
FIG. 15 is a schematic view of a sixth exemplary embodiment of a container of the present invention.

A sixth exemplary embodiment constructed in accordance with the present invention is illustrated in FIGS. 15 and 16. The embodiment shown in FIGS. 15 and 16 is substantially similar to the embodiment shown in FIGS. 13 and 14. Accordingly, the same reference numbers will be used to designate similar components in FIGS. 15 and 16. The container 500 includes a chamber 520 with an inlet 506. The container 500 may be rigid or flexible. A diverter 790 is present along the length of the container 500. The diverter 790 may be a rigid thermal-formed plastic diverter. The diverter 790 has a shape that protrudes from the wall 504 in the area of the sensor 510.

The diverter 790 has first and second connector portions 792 and 794. The connector portions 792 and 794 are connected to an inner surface 509 of the wall 504 of the container 500 on opposite sides of the sensor 510. The connector portions 792 and 794 may be connected to the wall 504 of the container 500 in any desired manner. A V-shaped portion 796 of the diverter 790 extends between the connector portions 792 and 794. The V-shaped portion 796 extends from the connector portions 792 and 794 into the chamber 520 so that the V-shaped portion is spaced from the sensor 510. The diverter 790 directs fluid flow to the bottom of the container 500 thereby preventing fluid from contacting the sensor 510. Accordingly, the diverter 790 prevents a temporary short from occurring between the elements 511 and 512 of the sensor 510 causing an erroneous fill measurement to be sensed. If the container 500 is flexible, the diverter 790 may prevent walls of the container from touching each other in the region of the sensor 510. Thus, the diverter 790 prevents an erroneous fill measurement to be sensed due to wall contact that may cause any fluids on the walls opposite the sensor 510 to contact the resistive elements of the sensor 510 resulting in the erroneous fill-level measurement conditions.

Figure 18:
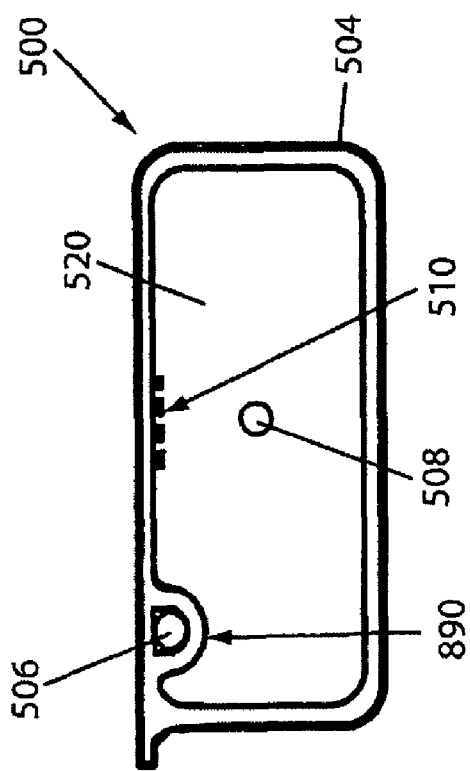
FIG. 18 is a schematic top view of the container of FIG. 17.
Figure 17:
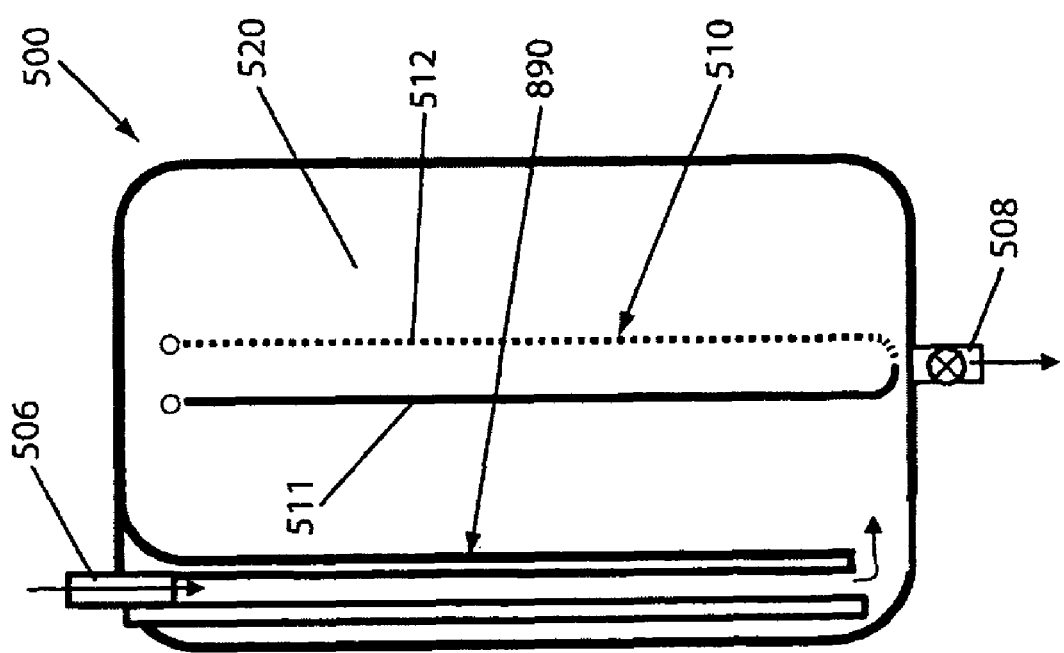
FIG. 17 is a schematic view of a seventh exemplary embodiment of a container of the present invention.

A seventh exemplary embodiment constructed in accordance with the present invention is illustrated in FIGS. 17 and 18. The embodiment shown in FIGS. 17 and 18 is substantially similar to the embodiment shown in FIGS. 13 and 14. Accordingly, the same reference numbers will be used to designate similar components in FIGS. 17 and 18. The container 500 includes a chamber 520 with an inlet 506. The container 500 may be rigid or flexible. A diverter 890, such as a wall defining a passage, extends along the length of the container 500. The diverter 890 extends from adjacent the inlet 506 toward the bottom of the container 500 and between the inlet and the sensor 510. The diverter 890 directs fluid flow to the bottom of the container 500 thereby preventing fluid from contacting the sensor 510. Accordingly, the diverter 890 prevents a temporary short from occurring between the elements 511 and 512 of the sensor 510 causing an erroneous fill measurement to be sensed. If the container 500 is flexible, the diverter 890 may prevent walls of the container from touching each other in the region of the sensor 510. Thus, the diverter 890 prevents an erroneous fill measurement to be sensed due to wall contact that may cause any fluids on the walls opposite the sensor 510 to contact the resistive elements of the sensor 510 resulting in the erroneous fill-level measurement conditions.

Figure 20:
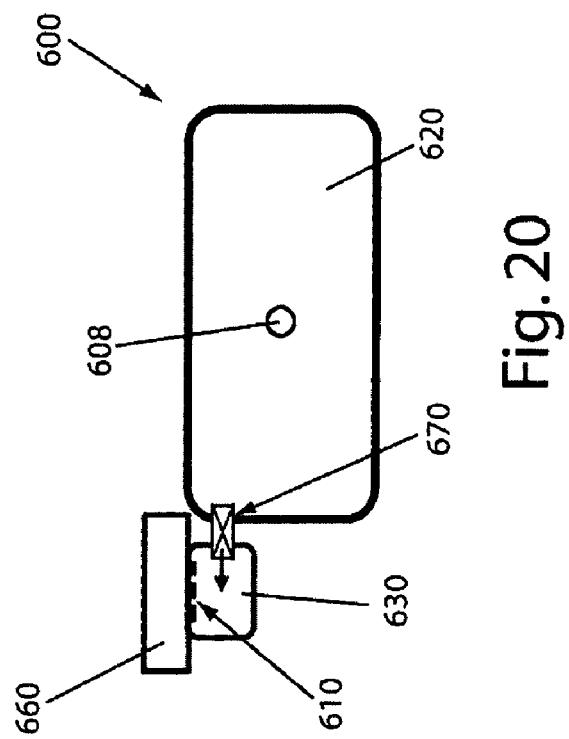
FIG. 20 is a schematic top view of the container of FIG. 19.
Figure 19:
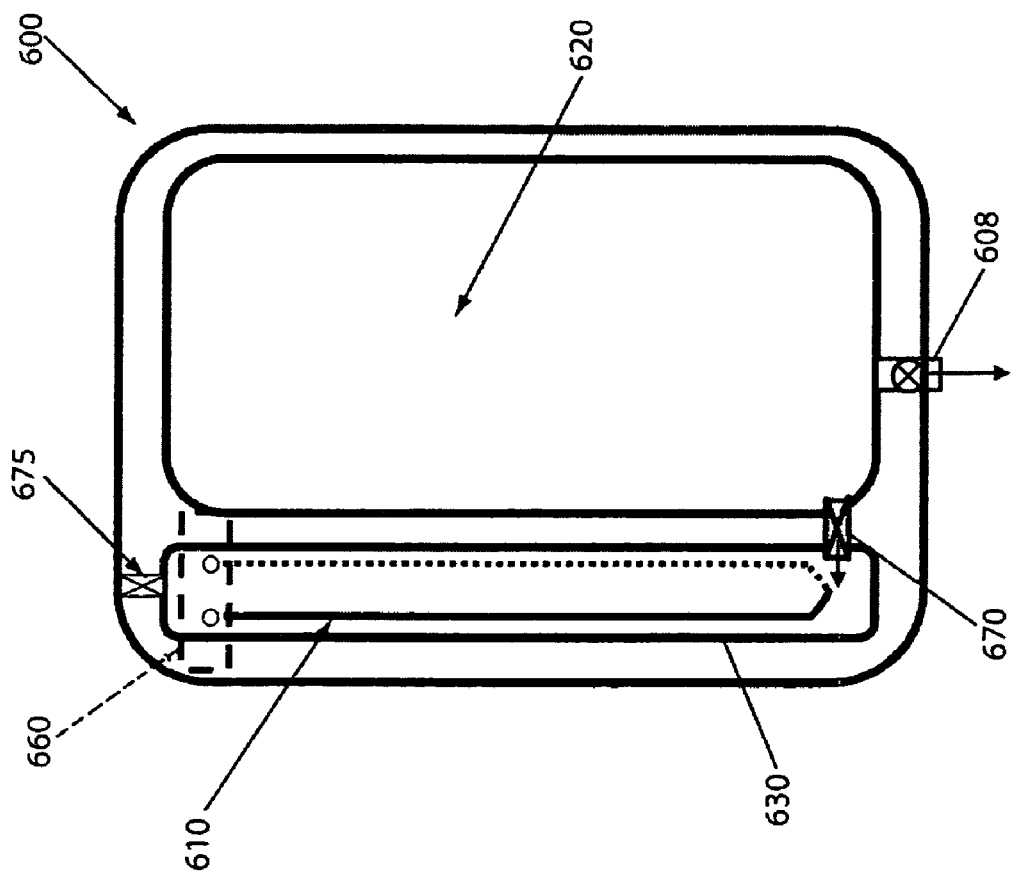
FIG. 19 is a schematic view of an eighth exemplary embodiment of a container of the present invention.

A container 600 constructed in accordance with an eighth exemplary embodiment constructed in accordance with the present invention is illustrated in FIGS. 19 and 20. The container 600 for storage and delivery of fluids, such as physiological fluids, has first and second chambers 620 and 630. The physiological fluid to be delivered may be saline solution, dextrose solution, therapeutic drugs mixed with physiological buffers, or blood. The fluid to be delivered is stored in the chamber 620. The container 600 includes an outlet valve 608 in communication with the chamber 620. The outlet valve 608 may be used to fill the chamber 620. Alternatively, the container 600 may also include an inlet port (not shown) in communication with the chamber 620 for filling the chamber.

A sensor 610 is located in chamber 630. The chamber 630 initially contains no fluid. The sensor 610 remains dry when no fluid is in the chamber 630. Prior to delivery of the physiological fluid to the patient through outlet valve 608, the fluid in chamber 620 is allowed to flow into chamber 630 by activating a closure member 670. The closure member 670 may be a valve or a removable plug. A vent 675 may allow any air trapped in chamber 630 to leave the chamber and, thereby, not impede filling of compartment 630 with fluid. Once the fluid flows into chamber 630, the sensor 610 monitors at least one characteristic of the fluid, such as fill level in the container

600 during fluid delivery. Contamination of the fluid by any potential leaching of sensor materials may be avoided.

A ninth exemplary embodiment constructed in accordance with the present invention is illustrated in FIGS. 21 and 22. The embodiment shown in FIGS. 21 and 22 is substantially similar to the embodiment shown in FIGS. 19 and 20. Accordingly, the same reference numbers will be used to designate similar components in FIGS. 21 and 22. The container 600 for storage and delivery of fluids, such as physiological fluids, includes an outlet vale 608. The container 600 has first and second chambers 620 and 630. The fluid to be delivered is stored in the chamber 620. The outlet valve 608 may be used for filling the chamber 620. The container 600 may also include an inlet port (not shown) in communication with the chamber 620 for filling the chamber.

A sensor 610 is located in chamber 630. The chamber 630 initially contains no fluid. The sensor 610 remains dry when no fluid is in the chamber 630. Prior to delivery of the physiological fluid to the patient through exit port 608, the fluid in chamber 620 is allowed to flow into compartment 630 by activating a closure member 770. The closure member 770 may be a zipper or an easy to break slit in the wall between the compartments. The closure member 770 extends from the top of the container 600 to the bottom of the container. Once the fluid flows into chamber 630, the sensor 610 monitors at least one characteristic of the fluid, such as fill level in the container 600 during fluid delivery. Contamination of the fluid by any potential leaching of sensor materials may be avoided.

Figure 24:
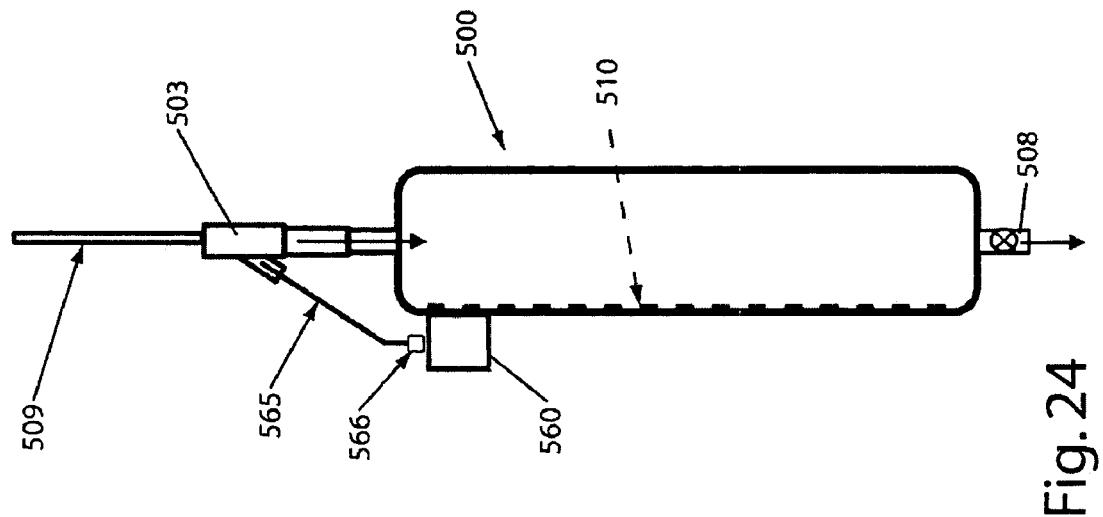
FIG. 24 is a schematic side view of the container of FIG. 23.
Figure 23:
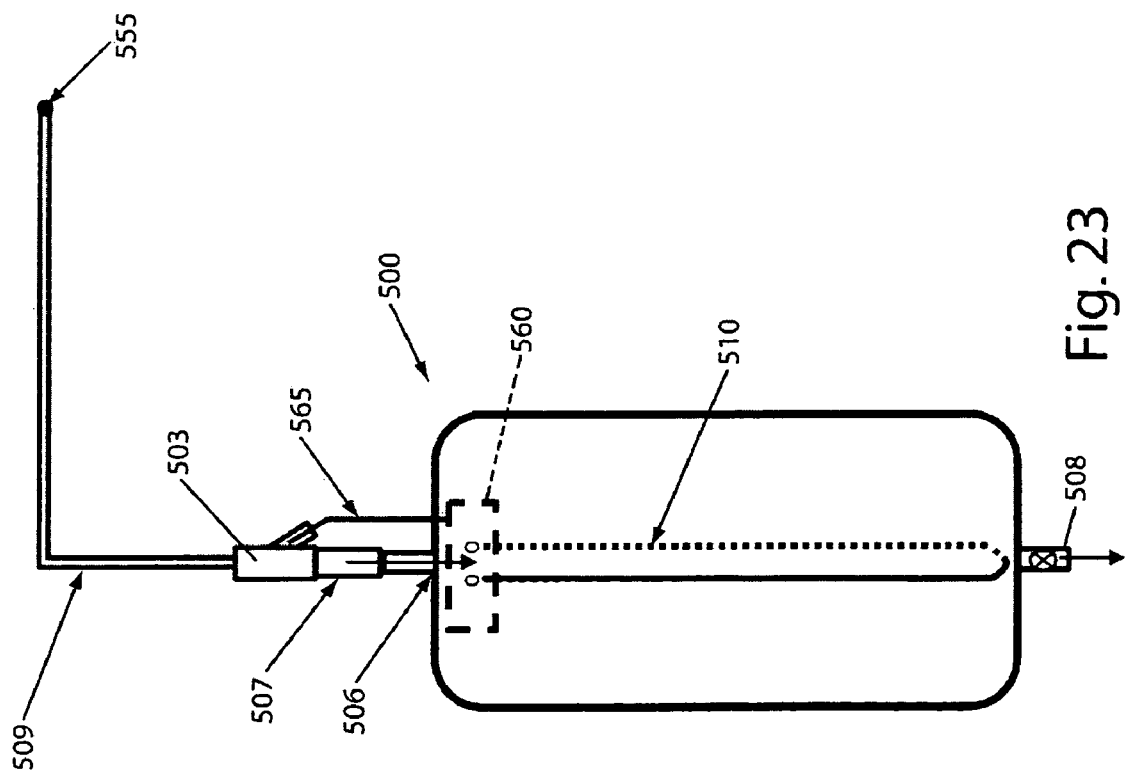
FIG. 23 is a schematic view of a tenth exemplary embodiment of a container of the present invention.

A tenth exemplary embodiment constructed in accordance with the present invention is illustrated in FIGS. 23 and 24. The embodiment shown in FIGS. 23 and 24 is substantially similar to the embodiment shown in FIGS. 13 and 14. Accordingly, the same reference numbers will be used to designate similar components in FIGS. 23 and 24. Core body temperature and/or pulse rate of a patient is a parameter that could be measured along with the characteristics of the fluid in a container. A urinary catheter 509 has a temperature sensor 555 (e.g., thermistor) formed at the catheter tip. The catheter may also include a microphone at the tip of the catheter to measure heart sounds that may indicate changes in pulse rate. The catheter tip and sensor 555 are placed within the bladder of a patient. The sensor 555 measures a patient's core body temperature and/or the microphone measures heart sounds.

At the proximal end of the catheter, there is an interface element 503 that allows an electrical cable 565 to connect the sensor 555 and/or the microphone to the electronic unit 560 using a connector element 566. Modifying the electronic circuit within the electronic unit 560 would allow wireless transmission of core body temperature and/or pulse rate along with other physiological parameters related to the collection container (e.g., urine fill level).

It is valuable to monitor characteristics, such as temperature, of the physiological fluid prior to and during delivery of that fluid to a patient. For example, blood collected and frozen must remain at a low temperature to retain its viability. If the blood is thawed and remains at room temperature for an extended period of time, the blood should no longer be transfused into a patient. In addition, drugs are often added to saline prior to infusion. After prolonged periods of exposure of the solubilized drug to room temperature conditions, the therapeutic performance of the drug can degrade.

Figure 25:
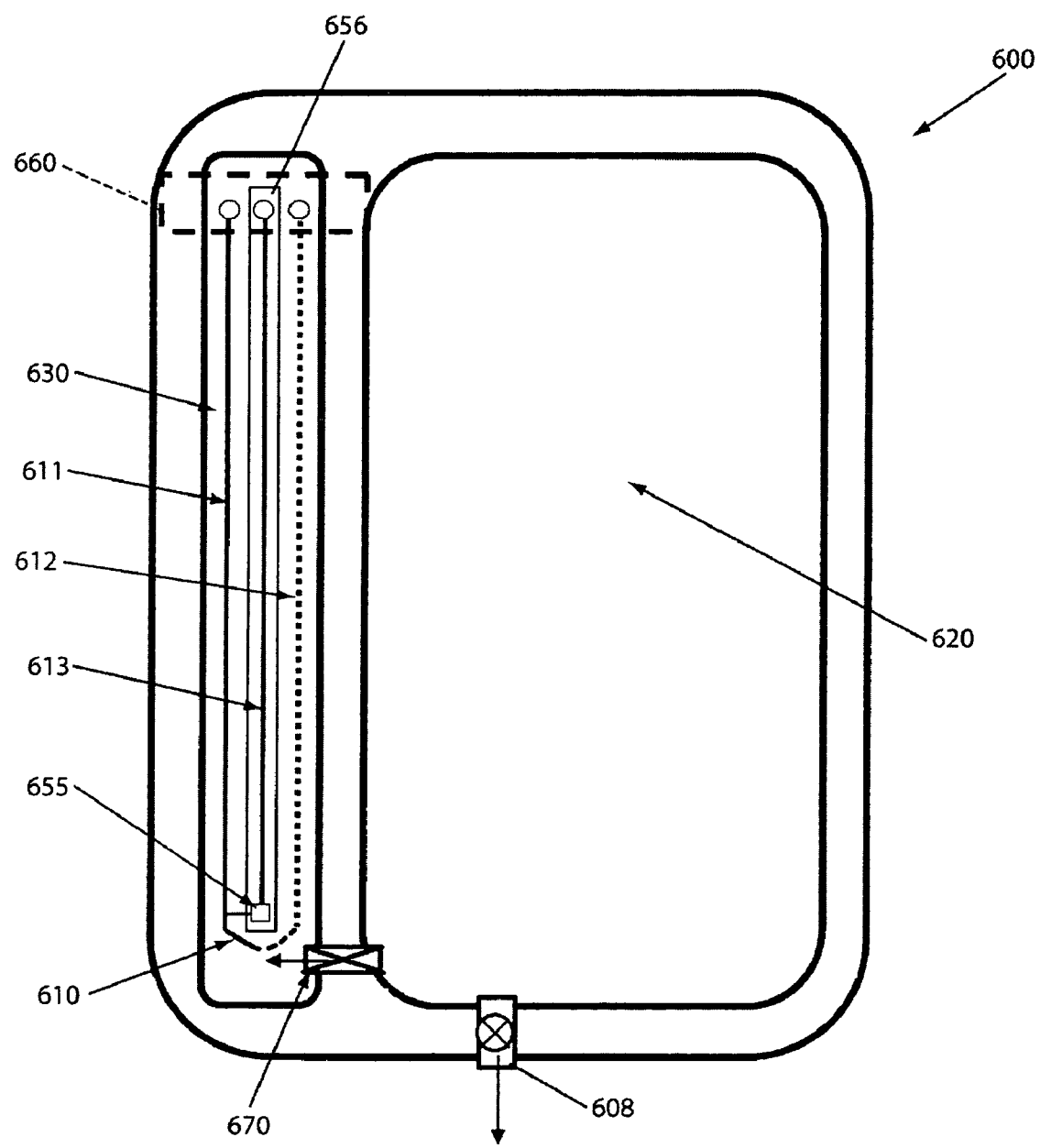
FIG. 25 is a schematic view of an eleventh exemplary embodiment of a container of the present invention.

An eleventh exemplary embodiment constructed in accordance with the present invention is illustrated in FIG. 25. The embodiment shown in FIG. 25 is substantially similar to the embodiment shown in FIGS. 19 and 20. Accordingly, the same reference numbers will be used to designate similar components in FIG. 25. The container 600 for storage and delivery of fluids, such as physiological fluids, has first and second chambers 620 and 630. The fluid to be delivered is stored in the chamber 620. The container 600 includes an outlet valve 608 in communication with the chamber 620. The outlet 608 may be used to fill the chamber 620. Alternatively, the container 600 may also include an inlet port (not shown) in communication with the chamber 620 for filling the chamber.

A first sensor 610 is located in chamber 630. The chamber 630 initially contains no fluid. The sensor 610 remains dry when no fluid is in the chamber 630. Prior to delivery of the physiological fluid to the patient through exit port 608, the fluid in chamber 620 is allowed to flow into compartment 630 by activating a closure member 670. The closure member 670 may be a valve or a removable plug. A vent (not shown) may allow any air trapped in chamber 630 to leave the chamber and, thereby, not impede filling of compartment 630 with physiological fluid. Once the fluid flows into chamber 630, the sensor 610 monitors at least one characteristic of the fluid, such as fill level in the container 600 during fluid delivery. An electronic unit 660 that attaches to the container 600 receives signals from the sensor 610. The electronic unit 660 transmits information to a remote unit (not shown) for display and analysis. Contamination of the fluid by any potential leaching of sensor materials may be avoided.

A second sensor 655 located in the chamber 630 may measure a characteristic of the fluid, such as fluid temperature. The sensor 655 is integrated into the electrode pattern of the sensor 610. Accordingly, the sensor 655 remains dry when no fluid is in the chamber 630. The sensor 610 includes elements 611 and 612. The sensor 655 is incorporated into the structure of the sensor 610 using a sensor element 613. The elements 611 and 613 are highly conductive (e.g. silver-based thin coating) and element 612 is carbon-based coating to provide a high resistance (e.g., 10,000 ohms/in). A coating 656 may seal the element 613 and sensor 655 from the fluid in chamber 630 to prevent shorting of the sensor 655 when physiological fluid contacts electrodes 611 and 612. The electronic unit 660 receives signals from the sensor 655. The electronic unit 660 transmits information to the remote unit (not shown) for display and analysis.

Figure 27:
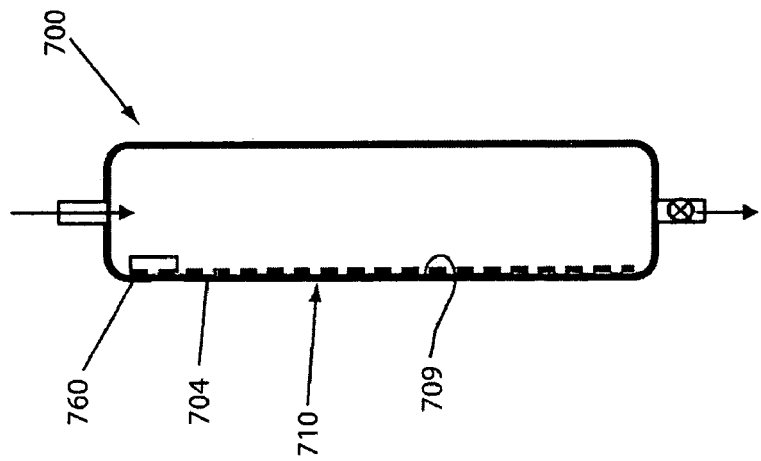
FIG. 27 is a schematic side view of the container of FIG. 26.
Figure 26:
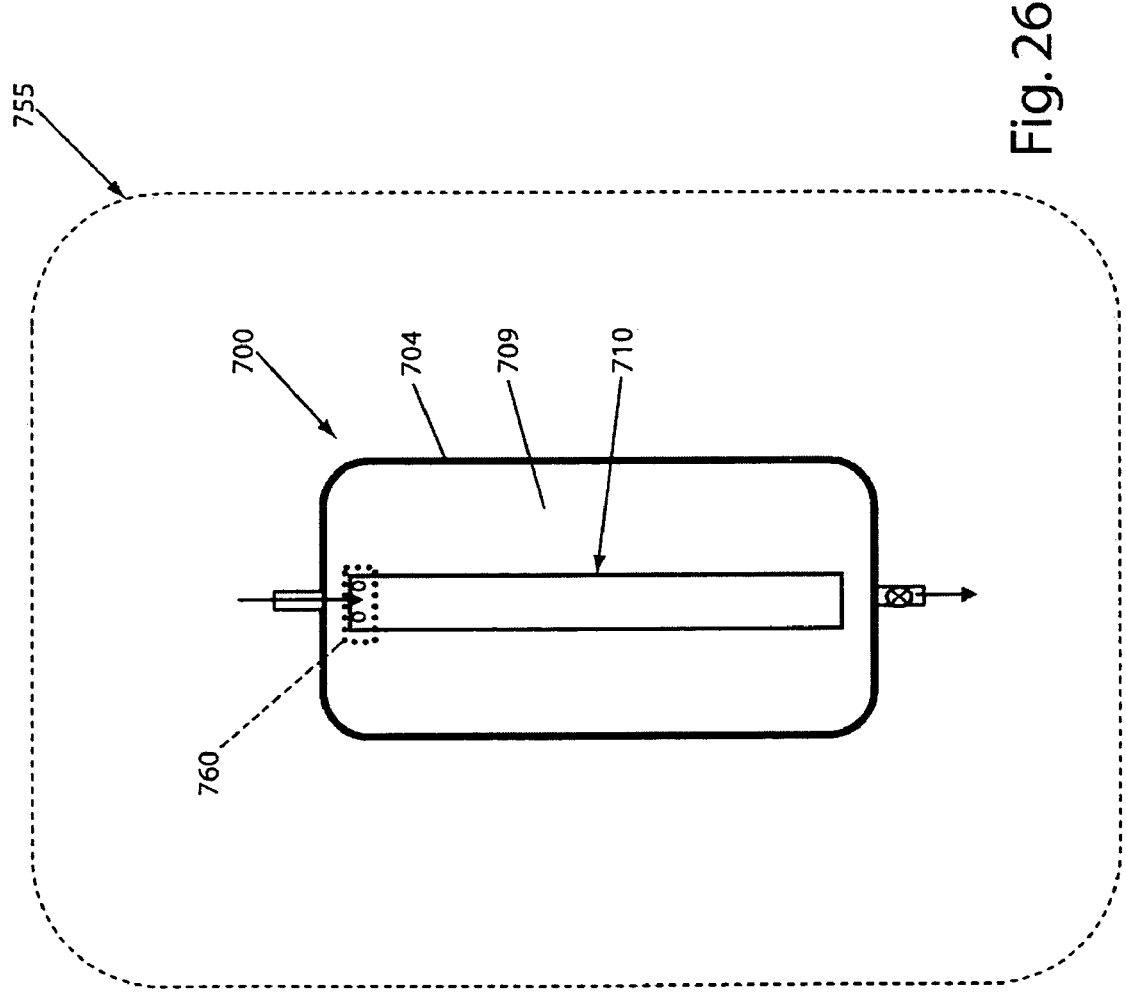
FIG. 26 is a schematic view of a twelfth exemplary embodiment of a container of the present invention.

The physiological fluid monitoring systems shown above involve attaching an electronic unit to the outside of the container. The unit communicates to remote devices via wireless communication methods. The unit monitors changes in physiological parameters of fluid in the containers by placing a sensor in the container and using electronic interface devices that communicate through the container walls. A container 700 constructed in accordance with a twelfth exemplary embodiment of the present invention is shown in FIGS. 26 and 27. The container 700 includes an electronic unit 760, such as a Radio Frequency Identification (RFID) tag, connected to an inner surface 709 of a wall 704 of the container. Internal interface elements (not shown) on unit 760 are in direct contact with a sensor 710. The electronic unit 760 may be disposed of along with the container and sensor 710. A sending/receiving antenna 755 interrogates the unit 760 and "reads-out" information from the unit. The unit 760 changes its output as a function of the output of the sensor 710. Antenna 755 is located in the area of interest (e.g., a patient's room).

The location of the container 700 may be determined using the unit 760 if the unit is an RFID tag. Alternatively, a Global Positioning System (GPS) chip may be connected into the standard electronic unit 560 to provide container location information.

As described above, fill level or volume of fluid is determined by sensing the resistance of a continuous resistor, such as a carbon-electrode resistor, of length, L, within the container. As the fluid level changes, more or less of the electrode height, h, along length L is shorted out by the fluid thereby changing the sensor resistance, Rs. Equation (10) below indicates that the change in resistance, ΔRs, for a given change in section length, ΔL, is written as follows:

$$\Delta Rs/\Delta L = R_{SQ}/W \qquad \text{Eq. (10)}$$

Where $R_{SQ}$ is a constant (i.e., resistance per square inch) for a resistor that may be made of a carbon ink used to print the electrode and W is the width of the electrode trace. Accordingly, the sensitivity of the sensor, ΔRs/ΔL, is inversely proportional to the sensor trace width, W.

The sensor may include two vertical electrodes or elements with a shunt resistor connecting the bottoms of the electrodes as described in U.S. Patent Application Publication No. 2006/0229575. The width of the electrodes of the sensor may be different at the bottom than at the top. The initial sensor resistance, Rs(0) is given by the following equation:

$$Rs(0) = 2Rv + Rst \qquad \text{Eq. (11)}$$

where Rv is the resistance of the vertical elements and Rst is the resistance of the shunt resistor. Using wider bottoms of the electrode traces decreases the sensitivity at the bottom of the sensor and makes the sensor more linear at the bottom of a flexible container. For flexible containers, the cross-sectional area of the container changes rapidly at the bottom so it is desirable to have the width of the electrode trace at the bottom relatively large. Conversely, a relatively small width for the vertical elements (i.e., smaller W) at the bottom of the sensor provides improved measurement accuracy (greater sensitivity due to greater resistance per unit length) over that region of the sensor length.

Figure 28:
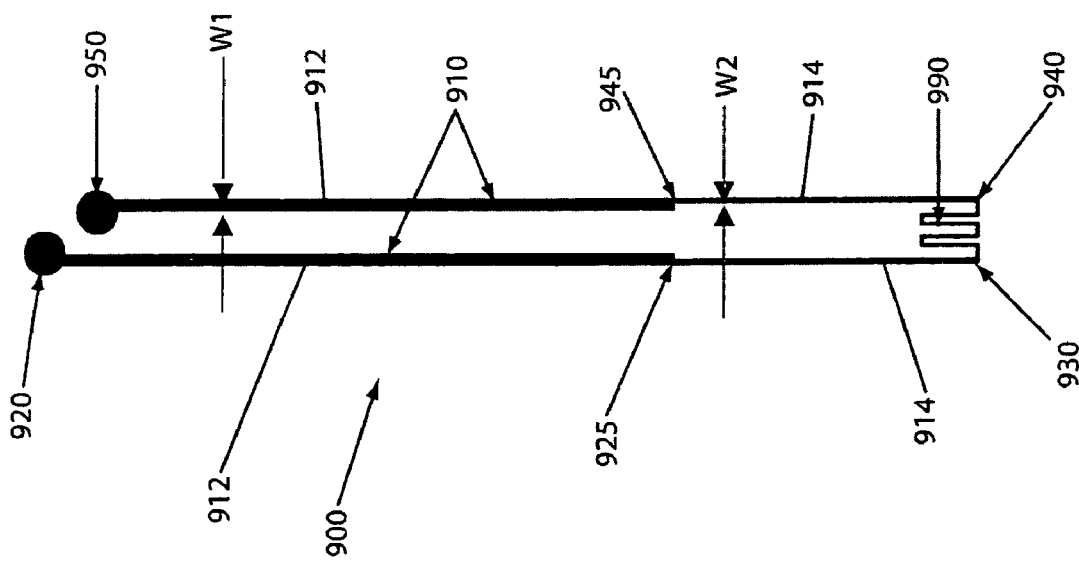
FIG. 28 is a schematic view of another sensor.

It is typical for patients to urinate at a flow rate of approximately 30 mL/hr so most patients will only fill a 2000 mL hospital/ICU urine collection container to approximately the 240 mL level during a standard 8-hour shift. It is desirable to determine accurate volumes for low container fill. An alternative sensor 900 for use in a container to sense the volume of fluid in the container is shown in FIG. 28. The sensor 900 includes first and second vertically extending elements 910. The elements 910 extend generally parallel to each other. Upper portions 912 of the elements 910 have widths W1. Lower portions 914 of the elements 910 have widths W2 smaller than the widths W1. A shunt resistor 990 connects the lower portions 914. The shunt resistor 990 may have a serpentine shape to provide an adequate length for a relatively large resistance of the shunt resistor Each of the upper portions 912 has a resistances Rv(1) measured from point 920 to 925 and point 950 to 945. Each of the lower portions 914 has a resistance Rv(2) measured from point 930 to 925 and point 940 to 945. The shunt resistor 990 has a resistance Rst measured from point 930 to point 940.

The initial resistance Rs(0) of the sensor 900 is written as follows:

$$Rs(0) = 2Rv(1) + 2Rv(2) + Rst \qquad \text{Eq. (12)}$$

The sensor 900 has relatively higher sensitivity at the bottom of the sensor since the resistance per unit length of the lower portions 914 is greater than the resistance per unit length of the upper portions 912. Accordingly, the sensor 900 is accurate for low volumes of fluid. It is contemplated that the upper portions 912 and the lower portions 914 of the elements 910 may have any desired resistance per unit length and the resistance per unit length of the elements 910 may not be the same. The resistance per unit length of the sensor elements 910 may vary in any desired manner along the length of the elements. For example, the resistance per unit length of the upper portions 912 of the sensor elements may be greater than the resistance per unit length of the lower portions if a greater sensitivity for the upper portions is desirable.

In the case of a container for use in the ICU, an accurate measurement of the volume of fluid in the container is desirable. The containers used in the ICU may be larger than portable containers. The bottom of a container may have a shape that causes a relatively large change in height (greater ΔL) for a relatively small amount of change in fluid volume ΔV. The accuracy may be greater if a change in height of the fluid is greater for a given change in fluid volume entering the container.

Figure 29:
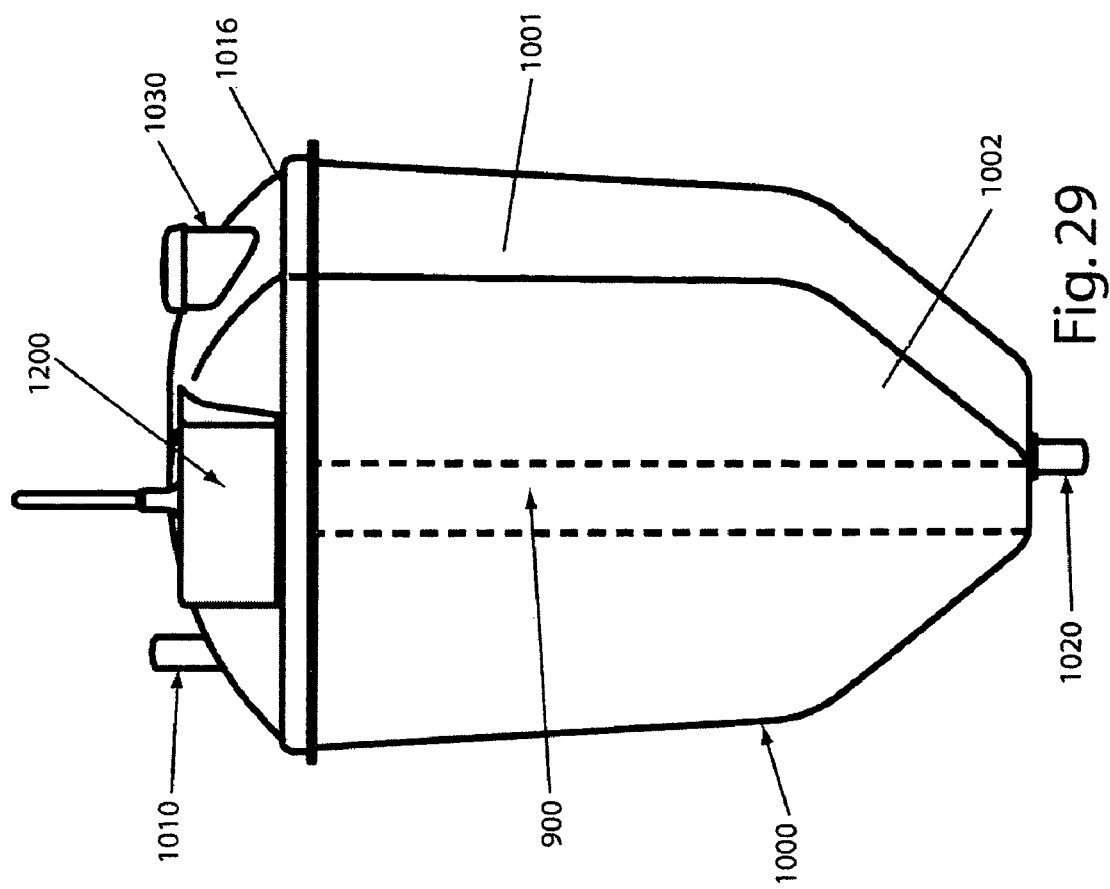
FIG. 29 is a schematic perspective view of a thirteenth exemplary embodiment of a container of the present invention.

A tenth embodiment of a container constructed in accordance with the present invention is shown in FIG. 29. The container 1000 may be a rigid container and may be disposable. The container 1000 includes the sensor 900 shown in FIG. 28 in contact with fluid in the container. The container 1000 (FIG. 29) includes an inlet port 1010 in a lid 1016 and an outlet valve 1020. The outlet valve 1020 may be used to allow fluids to flow from the container 1000 for disposal or for delivery to a patient.

The lid 1016 may include a vent 1030 that allows air to escape as fluid fills the container 1000. A special material may cover an opening in the vent 1030 that keeps collected fluid in the container 1000, as known in the art. An electronic interface/transmitter unit 1200 may be connected to the lid 1016 of the container 1000. The electronic unit 1200 is connected to the sensor 900 using disconnecting/reconnecting snap connectors (not shown). The electronic unit 1200 transmits container fill level information to an external receiver/analysis/display device (not shown) and may be reusable.

The container 1000 has an upper chamber 1001 and a lower chamber 1002. The upper chamber 1001 has a substantially constant cross-section. The lower chamber 1002 has a cross-section that increases linearly with height from the bottom of the container 1000. Accordingly, small increases in fluid volume entering the lower chamber 1002 result in larger increases in fluid height than in the top portion 1001. Therefore, the lower chamber 1002 of the container 1000 has higher measurement accuracy due to its shape.

The interface between the upper portions 912 and the lower portions 914 of the sensor 900 at locations 925 and 945 shown in FIG. 28 coincides with the interface between the upper and lower chambers 1001 and 1002 of container 1000. Accordingly, an even greater sensitivity, hence accuracy, is achieved.

For example if W2=W1÷2 the sensitivity of the bottom portion of the sensor 900 would be 2 times that of the top portion. If a 45 degree, inverted right triangular prism is used for the bottom chamber 1002 of the container 1000, in addition to the sensor 900, the sensitivity in the lower chamber 1002 of the container 1000 is approximately 3 times the sensitivity in the upper chamber 1001.

A continuous, carbon resistor sensor 900 was fabricated with the following characteristics:
  W1=0.08 inches (upper portion)
  W2=0.04 inches (lower portion)
  Length (upper portion)=8.5 inches corresponding to the height of the upper portion 1001 of the container 1000.
  Length (lower portion)=2.5 inches corresponding to the height of the lower, triangular portion 1002, of the container 1000.
  Rst=1.8 Kilo-ohms (K-ohms)
  Rs(0)=48 K-ohms giving a ratio Rst/R(0)=0.0375

The sensor 900 was placed in the container 1000 and connected to an electronic unit 1200 using commercially available mechanical snaps.

The container 1000 was then filled with known volumes of saline solution (0.09% NaCl) and the signal from an electronic unit 1200 was recorded for each volume added. The electronic signal was converted to a sensor resistance value, Rs, using a calibration obtained from known electrical resistors. The following sensor signal parameter was then calculated:

$$dRs/Rs(0)=100\cdot[Rs(0)-Rs]/Rs(0) \qquad \text{Eq. (13)}$$

Figure 30:
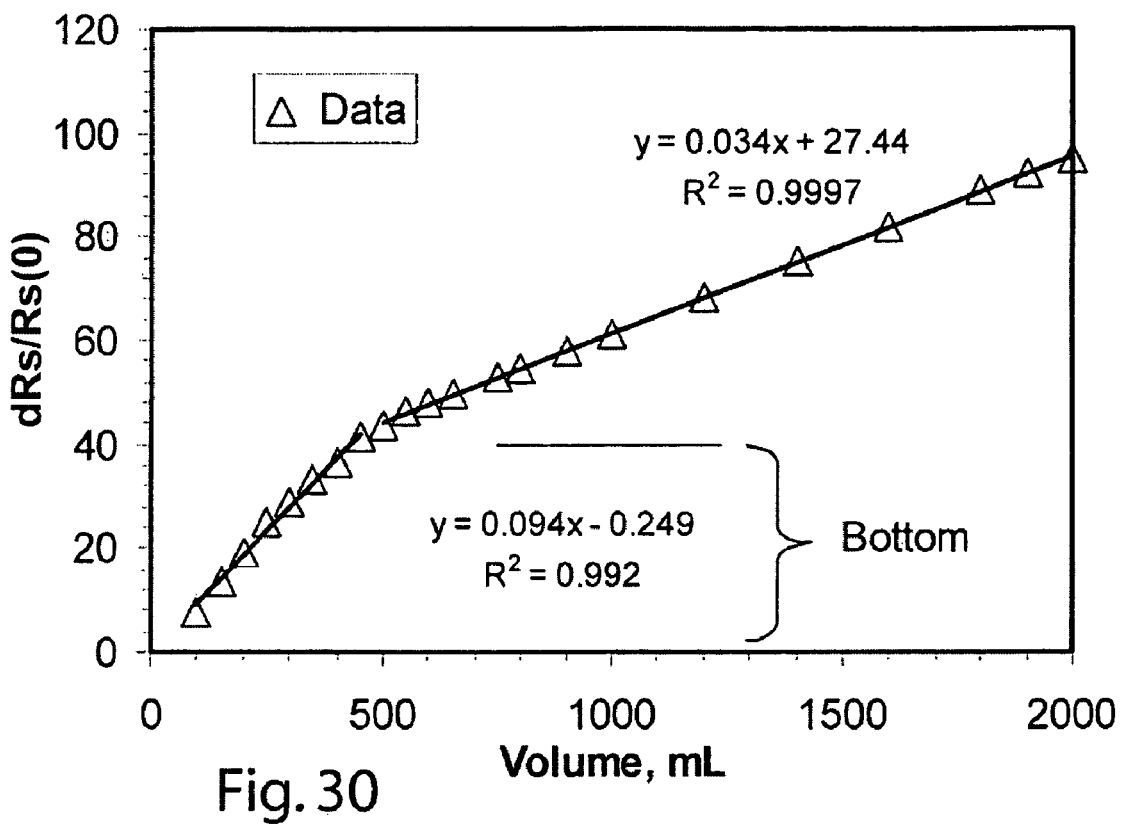
FIG. 30 is a graph showing signal output of the sensor of FIG. 28 as a function of volume of fluid in the container of FIG. 29.

It was found that performing the ratio of measured resistance difference divided by initial resistance (i.e., dRs/Rs(0)) in Eq (13) cancelled out the effect of sensor-to-sensor resistance variation (i.e., variations in Rs(0) that depended on manufacturing differences from one sensor to another). The ratio in Eq (13) was selected as the preferred sensor signal value and it was plotted as a function of the volume of fluid in container 1000. The sensor signal versus volume graph is shown in FIG. 30.

At relatively low container volumes (100 to 500 mL) the change in signal dRs/Rs(0) for a given 100 mL input fluid volume change was 2.76 times greater than the change in signal from 500 mL to 2000 mL for the same 100 mL input volume change (slope=0.094 compared to 0.034). This difference was approximately equal to the expected 3 times difference. The data in FIG. 30 demonstrates good fill measurement accuracy for collected fluid volumes greater than 100 mL.

The resistance Rst of the shunt resistor 990 relative to the initial sensor resistance (i.e. Rst/Rs(0)) also effects the sensitivity of the sensor 900 at the bottom of the sensor. The sensor signal versus volume experiment discussed above was modified by removing the sensor 900 from the container 1000 and measuring change in signal dRs/Rs(0) as a function of fill level height, h, above the bottom of the sensor trace. This modified experiment was performed for various resistance values Rst of the shunt resistor 990.

Figure 31:
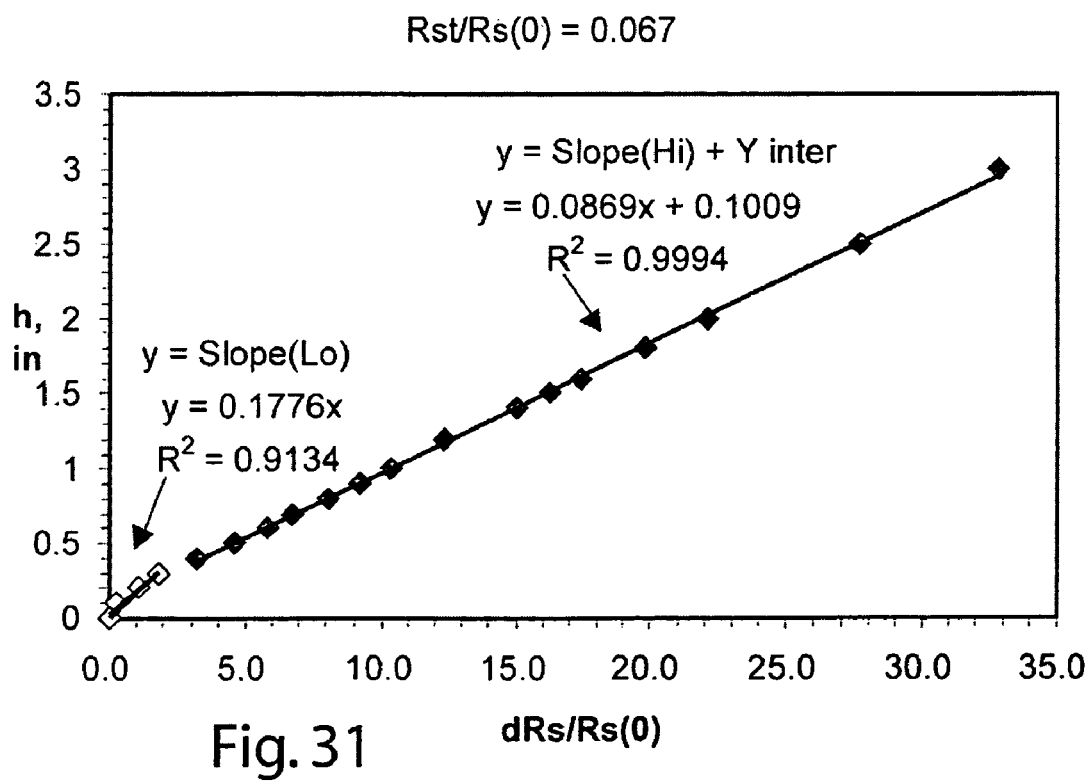
FIG. 31 is a graph showing sensor-determined fill level, h, as a function of the sensor-measured value for Rst/Rs(0) =0.067.

FIG. 31 shows a graph from one of these experiments where the ratio of shunt resistance to overall resistance Rst/Rs(0) was equal to 0.067. The height of the fluid is plotted as a function of the sensor signal dRs/Rs(0). The slope at the bottom of the sensor trace Slope(Lo) is different than the slope at the upper portion of the trace Slope(Hi). The very low volume signals become as sensitive as the intermediate volume signals as these slopes become approximately the same and the Y-intercept becomes approximately equal to zero.

Figure 32:
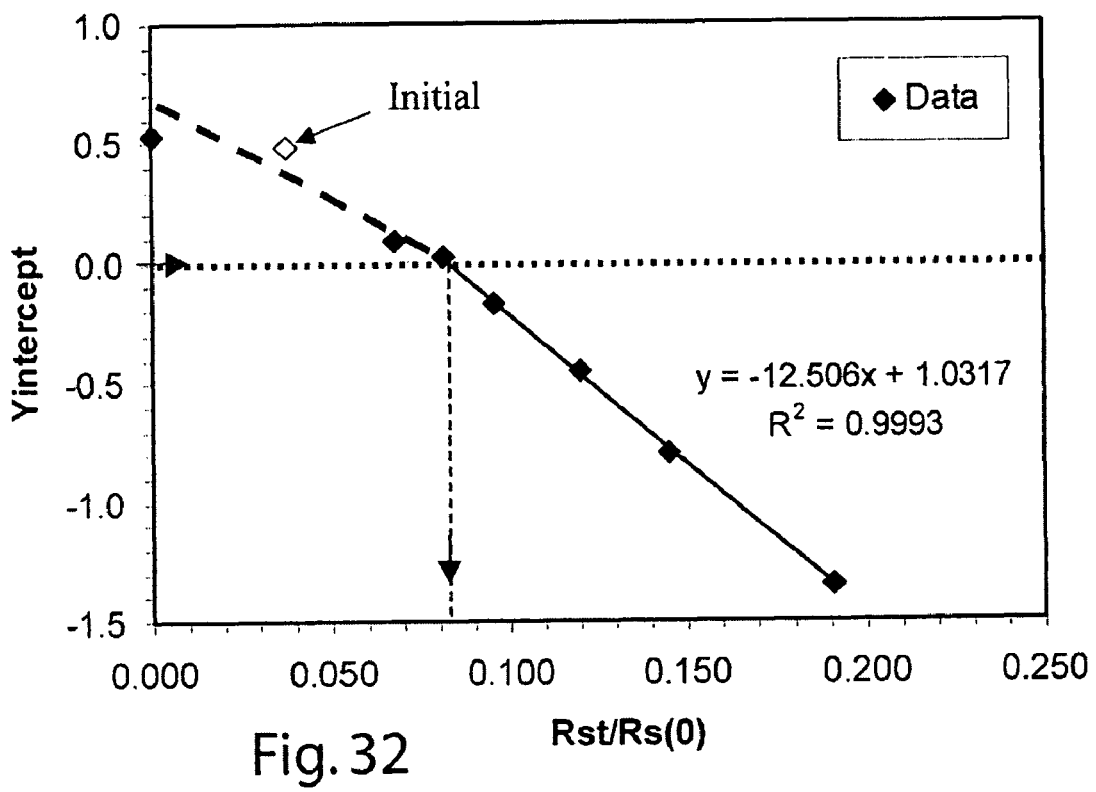
FIG. 32 is a graph showing Y-intercepts for various Rst/Rs (0) ratio values.

FIG. 32 shows a graph for calculating the optimum Rst/Rs(0) value by plotting the Y-intercept values for various Rst/Rs(0) values. Note in this figure that a value of Rst/Rs(0)≈0.083 provides the optimum shunt resistance-to-overall resistance value where the Y-intercept is approximately zero. A more accurate optimum resistance ratio value can be calculated using the linear fit shown in FIG. 32. Setting the equation to zero and calculating the optimum value, one gets 0.0824=1.03/12.5. The initial Y-intercept value for the initial sensor used to provide the data in FIG. 30 is also shown in FIG. 32. Note that the shut resistance-to overall resistance value was initially below the optimum value determined from the additional tests.

Figure 33:
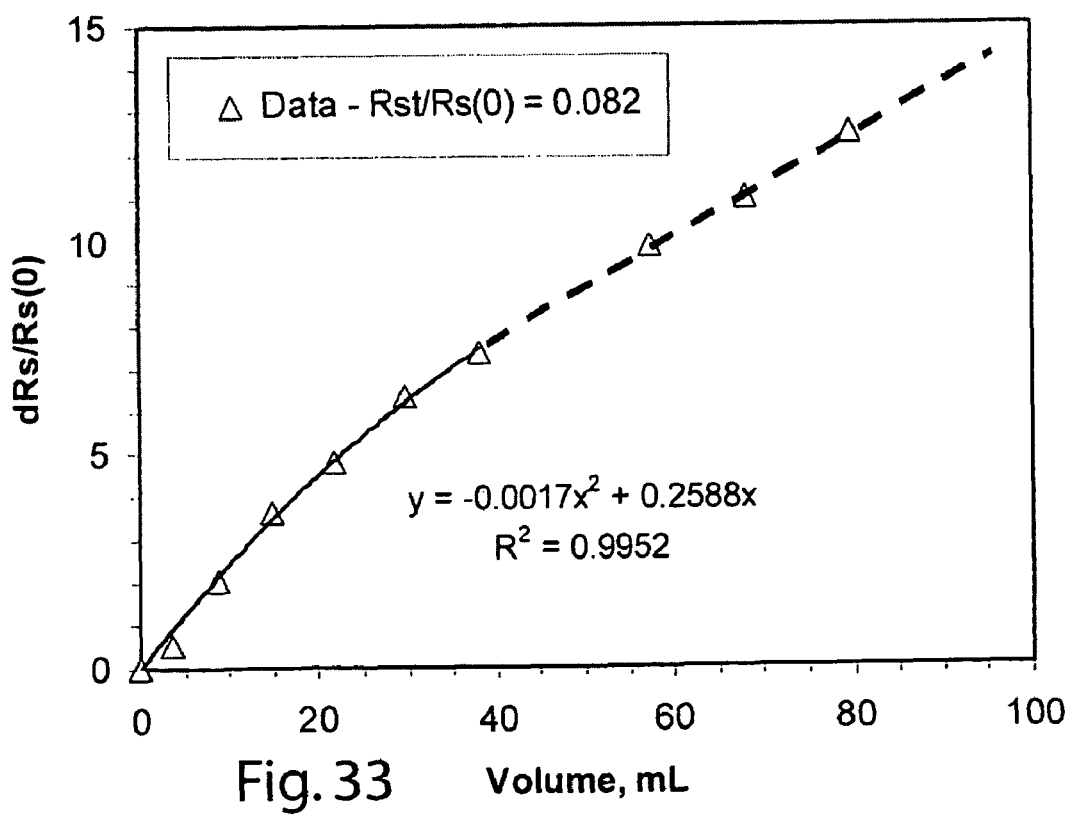
FIG. 33 is a graph showing the signal output of the sensor of FIG. 28 as a function of fluid volume for a sensor having a value of Rst/Rs(0)=0.082.

A sensor 900 as shown in FIG. 28 with a shunt resistance-to-overall resistance value of approximately 0.082 provides accurate volume sensing at all volumes from approximately zero mL to approximately 2000 mL. A demonstration of this accuracy for very low volumes is shown in FIG. 33, where the signal as a function of volume is shown plotted for container volumes from 0 to 80 mL. The sensitivity at collection volumes less that 50 mL is more desirable than the shunt resistance Rst was optimized.

In a typical hospital-use scenario, a collection container will be emptied periodically as it becomes full and/or when the nursing shift changes approximately every eight to twelve hours. In this case, the valve 1020 at the bottom of the container 1000 is opened and the collected fluid is drained into a measuring device (graduated cylinder) then discarded or it is discarded without measurement.

After fluid is emptied from the container 1000, it is desirable that the sensor 900 return to an initial zero volume resistance value Rs(0) as quickly as possible. If some fluid remains on the sensor 900 and/or between the electrodes 910, the fluid may temporarily short out the sensor. The shorting out of the sensor electrodes 910 may cause the sensor resistance value to be lower than the initial, dry sensor value Rs(0). The lower resistance value may result in the sensor indicating a small positive volume in the container even though the volume is approximately zero. Eventually, the fluid on the sensor 900 dries and the resistance returns to the initial resistance value Rs(0) and the indicated volume returns to zero. The lack of instantaneous return to zero volume conditions after emptying the container can lead to temporary sensor-readout errors. These errors can be problematic during urine collection, since protein in the urine tends to make the surfaces of the sensor 900 hydrophilic, whereby the urine may remain on the sensor 900 and not rapidly shed off or dry.

A coating made of a hydrophobic material may be placed on the sensor 900. The term hydrophobic material refers to a physical property of a material that results in water being repelled from (not adhering to) the material. Instead water forms droplets with a high contact angle and the water droplets tend to shed off such surfaces. Examples of hydrophobic materials are alkanes, oils, waxes, and silicones.

The coating may extend between the sensor electrodes 910. The hydrophobic coating repels water from the sensor 900 to minimize temporary shorting of the sensor after the container is emptied. The hydrophobic coating may be a moisture-curing silicone (GE Silicone II). The hydrophobic coating of a moisture-curing silicone that was approximately 0.3 inches wide and 0.005 inches thick was used between the carbon electrodes 910 having a 0.5-inch electrode separation. Table 1 shows that the hydrophobic coating improved recovery time by a factor of approximately five, to a value of less than 2 minutes.

TABLE 1

Sensor Response Improvement following container emptying

| | Recovery Time, minutes | |
|---|---|---|
| Coating | Saline solution | Urine |
| None | 5 | 10 |
| Silicone II coating | <1 | <2 |

Although different exemplary embodiments are described above, it is contemplated that components of the different embodiments may be used together or separately in other embodiments. For example, the sensor 900 and/or the diverters 690, 790, 890 may be used in any of the exemplary embodiments. The physiologic fluid in the containers may be urine, saline solution, dextrose solution, therapeutic drugs mixed with physiological buffers, or blood.

In view of the description above, those skilled in the art will become aware of modifications and changes which may be made in the present invention, and such modifications and changes are intended to be covered by the appended claims.

Having described the invention, the following is claimed:

1. A container for fluid comprising:
a chamber for containing fluid;
a sensor disposed within the chamber for sensing a property of fluid in the container;
a unit that receives a signal from the sensor and communicates with a device that displays the property of the fluid in the container, the sensor including a conductive element and a resistive element, the conductive element being made of a silver-particle-based material and the resistive element being made of a carbon-particle-based material.

2. A container for fluid comprising:
a chamber for containing fluid;
a sensor disposed within the chamber for sensing a property of fluid in the container;
a unit that receives a signal from the sensor and communicates with a device that displays the property of the fluid in the container, said container including a plurality of chambers having different volumes, the plurality of chambers being arranged so that fluid flows into the smallest chamber first and then fills subsequent larger volume chambers, a plurality of different length sensors sense the volume of fluid in each of the chambers, the fluid interacting with a shortest sensor of the plurality of sensors first and interacting with subsequent longer length sensors of the plurality of sensors in the subsequent larger volume chambers.

3. The container as set forth in claim 2 wherein the unit communicates wirelessly with the device that displays the property of the fluid.

4. The container as set forth in claim 2 wherein each sensor includes an element, the element including a resistive element.

5. The container as set forth in claim 4 wherein the resistive element is made of a carbon-particle-based material.

6. The container as set forth in claim 2 wherein the plurality of sensors sense the volume of fluid in the plurality of chambers independently of each other, each of the plurality of sensors having a conductive element and a resistive element.

7. The container as set forth in claim 2 wherein the sensor is being-formed by one of screen printing and ink-jet printing.

8. The container as set forth in claim 7 wherein the sensor is connected to a strip that is placed within the chamber of the container.

9. The container as set forth in claim 2 wherein the sensor is connected to an inner surface of a wall of the container.

10. The container as set forth in claim 2 the plurality of different volume chambers are stacked inside each other such that fluid fills a smallest chamber of the plurality of chambers first then overflows to fill a subsequent larger volume chamber through a flow passage, a plurality of different length sensors sensing the volume of fluid in each of the plurality of chambers, the fluid interacting with a shortest sensor of the plurality of sensors in the smallest volume chamber first, then interacting with a subsequent longer length sensor in a larger volume chamber.

11. The container as set forth in claim 2 wherein a diverter directs fluid flowing into the container and prevents the fluid from interacting with at least one of the sensors when the fluid flows into the container.

12. The container as set forth in claim 11 wherein the diverter includes a tube directing inlet fluid to a bottom of the container.

13. The container as set forth in claim 11 wherein the diverter includes a flow deflector inside that directs flow around the sensor.

14. The container as set forth in claim 11 wherein the diverter includes a channel formed in the container to direct fluid to the bottom of the container.

15. The container as set forth in claim 2 wherein said container includes a device to prevent fluid in the container from initially coming in contact with at least one of the sensors in such a way as to result in possible contamination of the fluid due to leaching of material from the sensor.

16. The container as set forth in claim 15 wherein the device is releasable prior to fluid delivery from the container to causes the fluid to interact with the sensor so that the sensor substrate can determine a property of the fluid.

17. The container as set forth in claim 16 wherein the device includes a valve in a wall between first and second chambers at a bottom of said container.

18. The container as set forth in claim 16 wherein the device includes a linear device extending along a length of first and second chambers.

19. The container as set forth in claim 2 wherein a catheter-tip sensor is connected to the unit.

20. The container as set forth in claim 19 wherein the catheter-tip sensor senses core body temperature.

21. The container as set forth in claim 19 wherein the catheter tip sensor senses fluctuations in internal pressure that may give an indication of one of patient heart rate and blood pressure.

22. The container as set forth in claim 2 wherein a temperature sensor is placed within the container to sense temperature of fluid within the container.

23. The container as set forth in claim 2 wherein a device is disposed within the container to communicate information to another device outside the container through a wall of the container.

24. The container as set forth in claim 23 wherein the device is an RFID tag.

25. The container as set forth in claim 23 wherein a loop of wire outside the container acts as an antenna to transmit and collect electronic signals from the device.

26. The container as set forth in claim 25 wherein the loop of wire is placed in at least one physical area of interest to determine where the container is physically located.

27. The container as set forth in claim 23 wherein an optical device is used to transmit light signals through a wall of the container that are received by an output device containing an optical detector.

28. The container as set forth in claim 2 wherein the container is a flexible bag.

29. The container as set forth in claim 2 wherein the container is a rigid container.

30. The container as set forth in claim 2 wherein a hydrophobic coating is located between first and second sensor elements of one of the sensors.

31. The container as set forth in claim 30 wherein the hydrophobic coating is one of a moisture-cured and ultraviolet-cured silicone rubber.

32. The container as set forth in claim 30 wherein the hydrophobic coating is a wax material.

33. A container for fluid comprising:
a chamber for containing fluid;
a sensor disposed within the chamber for sensing a property of fluid in the container;

a unit that receives a signal from the sensor and communicates with a device that displays the property of the fluid in the container, including a plurality of different volume chambers that are adjacent to each other such that fluid fills a smallest chamber of the plurality of chambers first, then overflows to fill a subsequent larger volume chamber through a flow passage, a plurality of different length sensors sensing the volume of fluid in each of the plurality of chambers, the fluid interacting with a shortest sensor of the plurality of sensors in the smallest volume chamber first, then interacting with a subsequent longer length sensor in a larger volume chamber.

34. A container for fluid comprising:
a chamber for containing fluid;
a sensor disposed within the chamber for sensing a property of fluid in the container;
a unit that receives a signal from the sensor and communicates with a device that displays the property of the fluid in the container, the sensor including an electrode trace with a smaller width at the bottom of the container to provide increased measurement sensitivity for low volumes of fluid entering the container, a shunt resistor having an optimum resistance connecting first and second electrode traces at a bottom of the sensor substrate to provide increased measurement sensitivity for very low volumes of fluid entering the container.

35. The container as set forth in claim 34 wherein the optimum resistance of the shunt resistor is determined by varying the shunt resistance relative to the overall sensor resistance to determine the optimum value that provides optimum sensor response at very low collection volumes.

36. The container as set forth in claim 35 wherein the optimum resistance is approximately 8 percent of the overall resistance of the sensor.

37. A container for fluid comprising:
a first chamber within the container for containing fluid;
a second chamber within the container for containing fluid;
a first sensor disposed within the first chamber, the first sensor being in contact with fluid in the first chamber, the first sensor sensing a volume of fluid in the first chamber; and
a second sensor disposed within the second chamber, the second sensor being in contact with fluid in the second chamber, the second sensor sensing a volume of fluid in the second chamber.

38. The container as set forth in claim 37 wherein the first chamber is smaller than the second chamber.

39. The container as set forth in claim 38 wherein the first chamber fills with fluid prior to the second chamber filling with fluid.

40. The container as set forth in claim 39 wherein the first chamber is below the second chamber when the container receives fluid.

41. The container as set forth in claim 37 wherein said first chamber is located within said second chamber, an orifice at the top portions of the first and second chambers connecting the first and second chambers.

42. A container for fluid comprising:
a first chamber for containing fluid;
a second chamber for containing fluid;
a first sensor disposed within the first chamber, the first sensor being in contact with fluid in the first chamber, the first sensor sensing a volume of fluid in the first chamber; and
a second sensor disposed within the second chamber, the second sensor being in contact with fluid in the second chamber, the second sensor sensing a volume of fluid in the second chamber, the first chamber being smaller than the second chamber, the first sensor extending along a length of the first chamber and the second sensor extending along a length of the second chamber, the first chamber and the first sensor being shorter than the second chamber and the second sensor.

43. A container for fluid comprising:
a first chamber for containing fluid;
a second chamber for containing fluid;
a first sensor disposed within the first chamber, the first sensor being in contact with fluid in the first chamber, the first sensor sensing a volume of fluid in the first chamber; and
a second sensor disposed within the second chamber, the second sensor being in contact with fluid in the second chamber, the second sensor sensing a volume of fluid in the second chamber, the first chamber being smaller than the second chamber.

44. A container for fluid comprising:
a first chamber for containing fluid;
a second chamber for containing fluid;
a first sensor disposed within the first chamber, the first sensor being in contact with fluid in the first chamber, the first sensor sensing a volume of fluid in the first chamber; and
a second sensor disposed within the second chamber, the second sensor being in contact with fluid in the second chamber, the second sensor sensing a volume of fluid in the second chamber, the first and second chambers being located adjacent each other, an orifice at top portions of the first and second chambers connecting the first and second chambers.

* * * * *